United States Patent [19]
Lok et al.

[11] Patent Number: 6,127,162
[45] Date of Patent: Oct. 3, 2000

[54] HUMAN PROHORMONE CONVERTASE 4

[75] Inventors: Si Lok, Seattle; Stephen R. Jaspers, Edmonds, both of Wash.

[73] Assignee: ZymoGenetics, Inc., Seattle, Wash.

[21] Appl. No.: 09/369,617

[22] Filed: Aug. 6, 1999

Related U.S. Application Data

[62] Division of application No. 09/071,101, May 1, 1998, Pat. No. 6,013,503.
[60] Provisional application No. 60/044,015, May 6, 1997.
[51] Int. Cl.[7] .............. C12N 9/64; C12N 1/20; C12N 15/00; C07H 21/04
[52] U.S. Cl. .......... 435/226; 536/23.2; 536/23.4; 435/252.3; 435/320.1
[58] Field of Search .................. 435/226, 252.3, 435/320.1; 536/23.2, 23.4

[56] References Cited

FOREIGN PATENT DOCUMENTS 2088222  4/1994  Canada .
92/09698  6/1992  WIPO .

OTHER PUBLICATIONS

Seidah et al., *Biochimie* 76: 197–209, 1994.
Smeekens, *Bio/Technology* 11: 182–196, 1993.
Nakayama et al., *J. Biol. Chem.* 267: 5897–5900, 1992.
Seidah et al., *Molecular Endocrinology* 6: 1559–1570, 1992.
Mbikay et al, *Genomics* 26: 123–129, 1996.
Mbikay et al., *Genomics* 20: 231–237, 1994.

*Primary Examiner*—Karen Cochrane Carlson
*Assistant Examiner*—Devesh Srivastava
*Attorney, Agent, or Firm*—Jennifer K. Johnson

[57] ABSTRACT

The present invention provides polynucleotide and polypeptide molecules for a novel human prohormone convertase 4. The polynucleotides encoding human prohormone convertase 4, are located on chromosome 19, and may, for example, be used to identify a region of the genome associated with human disease states. The present invention also includes methods for producing the protein and antibodies thereto.

12 Claims, 3 Drawing Sheets

```
Human PC1     MERRAWSLQCTAFVL FCAWCALNSAKAKRQ FVNEWAAEIPGGPEA ASAIAEELGYDLLGQ    60
Human PC2     MKGGCVSQWKAAAGF LFCVMVFASAERPVF TNHFLVELHKGGEDK ARQVAAEHGFGVRKL    60
Rat PC4       -------MRPSQTAL WLGLVLSLALLAVGW ASARPPIYVSSWAVR VTKGYQEAERLARKF    53
Murine PC4    -------MRPSQTEL WLGLTLTLALLAVRW ASAQAPIYVSSWAVR VTKGYQEAERLARKF    53
Human PC4     ----MRPAPIALWLR LVLALALVRPRAVGW APVRAPIYVSSWAVQ VSQGNREVERLARKF    56
Murine Furin  --------MELRSWL LWVVAAAGAVVLLAA DAQGQKIFTNTWAVH IPGGPAVADRVAQKH    52
Human Furin   --------MELRPWL LWVVAATGTLVLLAA DAQGQKVFTNTWAVR IPGGPAVANSVARKH    52

Human PC1     IGSLENHYLFKHKNH PRRSRRSAFHITKRL SDDDR----VIWAEQ QYEKERSKRSALRDS   116
Human PC2     PFAEGLYHFYHNGLA KAKRRRSLHHKQQLE RDPRV----KMALQQ EGFDRKKRGYRDINE   116
Rat PC4       GFVNLGQIFPDDQYF HLRHRGVAQQSLTPH WGHRL---RLKKEPK VRWFEQQTLRRRVKR   110
Murine PC4    GFVNLGQIFPDNQYF HLRHRGVAQQSLTPH WGHPL---RLKKDPK VRWFEQQTLRRRVKR   110
Human PC4     GFVNLGPIFPDGQYF HLRHRGVQQSLTPH WGHRL---HLKKNPK VQWFQQQTLQRRVKR   113
Murine Furin  GFHNLGQIFGDYYHF WHRAVTKRSLSPHRP RHSRL----QREPQV KWLEQQVAKRRAKRD   108
Human Furin   GFLNLGQIFGDYYHF WHRGVTKRSLSPHRP RHSRL----QREPQV QWLEQQVAKRRTKRD   108

Human PC1     ALNLFNDPMWNQQWY LQDTRMTAALPKLDL HVIPVWQKGITGKGV VITVLDDGLEWNHTD   176
Human PC2     IDINMNDPLFTKQWY LINTGQADGTPGLDL NVAEAWELGYTGKGV TIGIMDDGIDYLHPD   176
Rat PC4       SLVVPTDPWFSKQWY MN------KEIEQDL NILKVWNQGLTGRGV VVSILDDGIEKDHPD   164
Murine PC4    SLVVPTDPWFSKQWY MN------KEIQQDL NILKAWNQGLTGRGV VISILDDGIEKDHPD   164
Human PC4     SVVVPTDPWFSKQWY MN------SEAQPDL SILQAWSQGLSGQGI VVSVLDDGIEKDHPD   167
Murine Furin  VYQEPTDPKFPQQWY LS------GVTQRDL NVKEAWAQGFTGHGI VVSILDDGIEKNHPD   162
Human Furin   VYQEPTDPKFPQQWY LS------GVTQRDL NVKAAWAQGYTGHGI VVSILDDGIEKNHPD   162

Human PC1     IYANYDPEASYDFND NDHDPFPRYDPTNEN KHGTRCAGEIAMQAN NHKCGVGVAYNSKVG   236
Human PC2     LASNYNAEASYDFSS NDPYPYPRYTDDWFN SHGTRCAGEVSAAAN NNICGVGVAYNSKVA   236
Rat PC4       LWANYDPLASYDFND YDPDPQPRYTPNDEN RHGTRCAGEVSATAN NGFCGAGVAFNARIG   224
Murine PC4    LWANYDPLASYDFND YDPDPQPRYTPNDEN RHGTRCAGEVSATAN NGFCGAGVAFNARIG   224
Human PC4     LWANYDPLASYDFND YDPDPQPRYTPSKEN RHGTRCAGEVAAMAN NGFCGVGVAFNARIG   227
Murine Furin  LAGNYDPGASFDVND QDPDPQPRYTQMNDN RHGTRCAGEVAAVAN NGVCGVGVAYNARIG   222
Human Furin   LAGNYDPGASFDVND QDPDPQPRYTQMNDN RHGTRCAGEVAAVAN NGVCGVGVAYNARIG   222

Human PC1     GIRMLDG-IVTDAIE ASSIGFNPGHVDIYS ASWGPNDDGKTVEGP GRLAQKAFEYGVKQG   295
Human PC2     GIRMLDQPFMTDIIE ASSISHMPQLIDIYS ASWGPTDNGKTVDGP RDVTLQAMADGVNKG   296
Rat PC4       GVRMLDG-AITDIVE AQSLSLQPQHIHIYS ASWGPEDDGRTVDGP GLLTQEAFRRGVTKG   283
Murine PC4    GVRMLDG-AITDIVE AQSLSLQPQHIHIYS ASWGPEDDGRTVDGP GLLT---------G   273
Human PC4     GVRMLDG-TITDVIE AQSLSLQPQHIHIYS ASWGPEDDGRTVDGP GILTREAFRRGVTKG   286
Murine Furin  GVRMLDG-EVTDAVE ARSLGLNPNHIHIYS ASWGPEDDGKTVDGP ARLAEEAFFRGVSQG   281
Human Furin   GVRMLDG-EVTDAVE ARSLGLNPNHIHIYS ASWGPEDDGKTVDGP ARLAEEAFFRGVSQG   281

Human PC1     RQGKGSIFVWASGNG GRQGDNCDCDGYTDS IYTISISSASQQGLS PWYAEKCSSTLATSY   355
Human PC2     RGGKGSIYVWASGDG GSY-DDCNCDGYASS MWTISINSAINDGRT ALYDESCSSTLASTF   355
Rat PC4       RQGLGTLFIWASGNG GLHYDNCNCDGYTNS IHTLSVGSTTRQGRV PWYSEACASTFTTTF   343
Murine PC4    RQGLGTLFIWASGNG GLHYDNCNCDGYTNS IHTLSVGSTTRQGRV PWYSEACASTFTTTF   333
Human PC4     RGGLGTLFIWASGNG GLHYDNCNCDGYTNS IHTLSVGSTTQQGRV PWYSEACASTLTTTY   346
Murine Furin  RGGLGSIFVWASGNG GREHDSCNCDGYTNS IYTLSISSATQFGNV PWYSEACSSTLATTY   341
Human Furin   RGGLGSIFVWASGNG GREHDSCNCDGYTNS IYTLSISSATQFGNV PWYSEACSSTLATTY   341
```

```
Human PC1     MERRAWSLQCTAFVL FCAWCALNSAKAKRQ FVNEWAAEIPGGPEA ASAIAEELGYDLLGQ    60
Human PC2     MKGGCVSQWKAAAGF LFCVMVFASAERPVF TNHFLVELHKGGEDK ARQVAAEHGFGVRKL    60
Rat PC4       -------MRPSQTAL WLGLVLSLALLAVGW ASARPPIYVSSWAVR VTKGYQEAERLARKF    53
Murine PC4    -------MRPSQTEL WLGLTLTLALLAVRW ASAQAPIYVSSWAVR VTKGYQEAERLARKF    53
Human PC4     ----MRPAPIALWLR LVLALALVRPRAVGW APVRAPIYVSSWAVQ VSQGNREVERLARKF    56
Murine Furin  --------MELRSWL LWVVAAAGAVVLLAA DAQGQKIFTNTWAVH IPGGPAVADRVAQKH    52
Human Furin   --------MELRPWL LWVVAATGTLVLLAA DAQGQKVFTNTWAVR IPGGPAVANSVARKH    52

Human PC1     IGSLENHYLFKHKNH PRRSRRSAFHITKRL SDDDR----VIWAEQ QYEKERSKRSALRDS   116
Human PC2     PFAEGLYHFYHNGLA KAKRRRSLHHKQQLE RDPRV----KMALQQ EGFDRKKRGYRDINE   116
Rat PC4       GFVNLGQIFPDDQYF HLRHRGVAQQSLTPH WGHRL---RLKKEPK VRWFEQQTLRRRVKR   110
Murine PC4    GFVNLGQIFPDNQYF HLRHRGVAQQSLTPH WGHPL---RLKKDPK VRWFEQQTLRRRVKR   110
Human PC4     GFVNLGPIFPDGQYF HLRHRGVQQSLTPH  WGHRL---HLKKNPK VQWFQQQTLQRRVKR   113
Murine Furin  GFHNLGQIFGDYYHF WHRAVTKRSLSPHRP RHSRL----QREPQV KWLEQQVAKRRAKRD   108
Human Furin   GFLNLGQIFGDYYHF WHRGVTKRSLSPHRP RHSRL----QREPQV QWLEQQVAKRRTKRD   108

Human PC1     ALNLFNDPMWNQQWY LQDTRMTAALPKLDL HVIPVWQKGITGKGV VITVLDDGLEWNHTD   176
Human PC2     IDINMNDPLFTKQWY LINTGQADGTPGLDL NVAEAWELGYTGKGV TIGIMDDGIDYLHPD   176
Rat PC4       SLVVPTDPWFSKQWY MN------KEIEQDL NILKVWNQGLTGRGV VVSILDDGIEKDHPD   164
Murine PC4    SLVVPTDPWFSKQWY MN------KEIQQDL NILKAWNQGLTGRGV VISILDDGIEKDHPD   164
Human PC4     SVVVPTDPWFSKQWY MN------SEAQPDL SILQAWSQGLSGQGI VVSVLDDGIEKDHPD   167
Murine Furin  VYQEPTDPKFPQQWY LS------GVTQRDL NVKEAWAQGFTGHGI VVSILDDGIEKNHPD   162
Human Furin   VYQEPTDPKFPQQWY LS------GVTQRDL NVKAAWAQGYTGHGI VVSILDDGIEKNHPD   162

Human PC1     IYANYDPEASYDFND NDHDPFPRYDPTNEN KHGTRCAGEIAMQAN NHKCGVGVAYNSKVG   236
Human PC2     LASNYNAEASYDFSS NDPYPYPRYTDDWFN SHGTRCAGEVSAAAN NNICGVGVAYNSKVA   236
Rat PC4       LWANYDPLASYDFND YDPDPQPRYTPNDEN RHGTRCAGEVSATAN NGFCGAGVAFNARIG   224
Murine PC4    LWANYDPLASYDFND YDPDPQPRYTPNDEN RHGTRCAGEVSATAN NGFCGAGVAFNARIG   224
Human PC4     LWANYDPLASYDFND YDPDPQPRYTPSKEN RHGTRCAGEVAAMAN NGFCGVGVAFNARIG   227
Murine Furin  LAGNYDPGASFDVND QDPDPQPRYTQMNDN RHGTRCAGEVAAVAN NGVCGVGVAYNARIG   222
Human Furin   LAGNYDPGASFDVND QDPDPQPRYTQMNDN RHGTRCAGEVAAVAN NGVCGVGVAYNARIG   222

Human PC1     GIRMLDG-IVTDAIE ASSIGFNPGHVDIYS ASWGPNDDGKTVEGP GRLAQKAFEYGVKQG   295
Human PC2     GIRMLDQPFMTDIIE ASSISHMPQLIDIYS ASWGPTDNGKTVDGP RDVTLQAMADGVNKG   296
Rat PC4       GVRMLDG-AITDIVE AQSLSLQPQHIHIYS ASWGPEDDGRTVDGP GLLTQEAFRRGVTKG   283
Murine PC4    GVRMLDG-AITDIVE AQSLSLQPQHIHIYS ASWGPEDDGRTVDGP GLLT----------G   273
Human PC4     GVRMLDG-TITDVIE AQSLSLQPQHIHIYS ASWGPEDDGRTVDGP GILTREAFRRGVTKG   286
Murine Furin  GVRMLDG-EVTDAVE ARSLGLNPNHIHIYS ASWGPEDDGKTVDGP ARLAEEAFFRGVSQG   281
Human Furin   GVRMLDG-EVTDAVE ARSLGLNPNHIHIYS ASWGPEDDGKTVDGP ARLAEEAFFRGVSQG   281

Human PC1     RQGKGSIFVWASGNG GRQGDNCDCDGYTDS IYTISISSASQQGLS PWYAEKCSSTLATSY   355
Human PC2     RGGKGSIYVWASGDG GSY-DDCNCDGYASS MWTISINSAINDGRT ALYDESCSSTLASTF   355
Rat PC4       RQGLGTLFIWASGNG GLHYDNCNCDGYTNS IHTLSVGSTTRQGRV PWYSEACASTFTTTF   343
Murine PC4    RQGLGTLFIWASGNG GLHYDNCNCDGYTNS IHTLSVGSTTRQGRV PWYSEACASTFTTTF   333
Human PC4     RGGLGTLFIWASGNG GLHYDNCNCDGYTNS IHTLSVGSTTQQGRV PWYSEACASTLTTTY   346
Murine Furin  RGGLGSIFVWASGNG GREHDSCNCDGYTNS IYTLSISSATQFGNV PWYSEACSSTLATTY   341
Human Furin   RGGLGSIFVWASGNG GREHDSCNCDGYTNS IYTLSISSATQFGNV PWYSEACSSTLATTY   341
```

Fig. 1A

```
Human PC1      S--GGDYTDQRITSA DLHNDCTETHTGTSA SAPLAAGIFALALEA NPNLTWRDMQHLVVW    413
Human PC2      SNGRKRNPEAGVATT DLYGNCTLRHSGTSA AAPEAAGVFALALEA NLGLTWRDMQHLTVL    415
Rat PC4        SSGVVTDPQI--VTT DLHHQCTDKHTGTSA SAPLAAGMIALALEA NPLLTWRDLQHLVVR    401
Murine PC4     SSGVVTDPQI--VTT DLHHQCTDKHTGTSA SAPLAAGMIALALEA NPLLTWRDLQHLVVR    391
Human PC4      SSGVATDPQI--VTT DLHHGCTDQHTGTSA SAPLAAGMIALALEA NPFLTWRDMQHLVVR    404
Murine Furin   SSGNQNEKQI--VTT DLRQKCTESHTGTSA SAPLAAGIIALTLEA NKNLTWRDMQHLVVQ    399
Human Furin    SSGNQNEKQI--VTT DLRQKCTESHTGTSA SAPLAAGIIALTLEA NKNLTWRDMQHLVVQ    399

Human PC1      TSEYDPLAN---NPG WKKNGAGLMVNSRFG FGLLNAKALVDLADP RTWRSVPEKKECVVK    470
Human PC2      TSKRNQLHD--EVHQ WRRNGVGLEFNHLFG YGVLDAGA--MVKMA KDWKTVPERFHCVGG    471
Rat PC4        ASRPAQLQA----ED WRINGVGRQVSHHYG YGLLDAGL--LVDLA RVWLPTKPQKKCTIR    455
Murine PC4     ASRPAQLQA----ED WRINGVGRQVSHHYG YGLLDAGL--LVDLA RVWLPTKPQKKCAIR    445
Human PC4      ASKPAHLQA----ED WRTNGVGRQVSHHYG YGLLDAGL--LVDTA RTWLPTQPQRKCAVR    458
Murine Furin   TSKPAHLNA----DD WATNGVGRKVSHSYG YGLLDAGA--MVALA QNWTTVAPQRKCIVE    453
Human Furin    TSKPAHLNA----ND WATNGVGRKVSHSYG YGLLDAGA--MVALA QNWTTVAPQRKCIID    453

Human PC1      DNDFEPRALKANGEV IIEIPTRACEGQE-- NAIKSLEHVQFEATI EYSRRGDLHVTLTSA    528
Human PC2      SVQDPEKI-PSTGKL VLTLTTDACEGKE-- NFVRYLEHVQAVITV NATRRGDLNINMTSP    528
Rat PC4        VVHTPTPI---LPRM LVPKNVTVCCDGSRR RLIRSLEHVQVQLSL SYSRRGDLEIFLTSP    512
Murine PC4     VVHTPTPI---LPRM LVPKNVTACSDGSRR RLIRSLEHVQVQLSL SYSRRGDLEIFLTSP    502
Human PC4      VQSRPTPI---LPLI YIRENVSACAGLH-- NSIRSLEHVQAQLTL SYSRRGDLEISLTSP    513
Murine Furin   ILVEPKDI---GKRL EVRKAVTACLGEP-- NHITRLEHVQARLTL SYNRRGDLAIHLISP    508
Human Furin    ILTEPKDI---GKRL EVRKTVTACLGEP-- NHITRLEHAQARLTL SYNRRGDLAIHLVSP    508

Human PC1      AGTSTVLLAERERD- ---TSPNGFKNWDFM SVHTWGENPIGTWTL RITDMSGRIQN---E    581
Human PC2      MGTKSILLSRRPRD- --DDSKVGFDKWPFM TTHTWGEDARGTWTL ELGFVGSAPQK----    581
Rat PC4        MGTRSTLVAIRPLD- ---ISGQGYNNWIFM STHYWDEDPQGLWTL GLENKGYYYNT----    564
Murine PC4     MGTRSTLVAIRPLD- ---ISGQGYNNWIFM STHYWDEDPQGLWTL GLENKGYYFNT----    554
Human PC4      MGTRSTLVAIRPLD- ---VSTEGYNNWVFM STHFWDENPQGVWTL GLENKGYYFNT----    565
Murine Furin   MGTRSTLLAARPHD- ---YSADGFNDWAFM TTHSWDEDPAGEWVL EIENTSEANNY----    560
Human Furin    MGTRSTLLAARPHD- ---YSADGFNDWAFM TTHSWDEDPSGEWVL EIENTSEANNY----    560

Human PC1      GRIVNWKLILHGTSS QPEHMKQPRVYTSYN TVQNDRRGVEKMVDP GEEQPTQENPKENTL    641
Human PC2      GVLKEWTLMLHGTQS APYIDQVVRDYQSKL AMSKKEELEEELDEA VERSLKSILNKN1     638
Rat PC4        GTLYYCTLLLYGTAE DMTARPQTPQVTSCA HACAEGHRGAVPGKS LSPLHCGRTLPHLQQ    624
Murine PC4     GTLYYYTLLLYGTAE DMTARPQAPQVTSRA RACVQRDTEGLCQES HSPLSILAGLCLISS    614
Human PC4      GTLYRYTLLLYGTAE DMTARPTGPQVTS-- SACVQRDTEGLCQAC DGPAYILGQLCLAYC    623
Murine Furin   GTLTKFTLVLYGTA- -----PEGLSTPPES SGCKTLTSSQACVVC EEGYSLHQKSCVQHC    614
Human Furin    GTLTKFTLVLYGTA- -----PEGLPVPPES SGCKTLTSSQACVVC EEGFSLHQKSCVQHC    614

Human PC1      VSKSPSSSSVGGRRD ELEEGAPSQAMLRLL QSAFSKNSPPKQSPK KSPSAKLNIPYENFY    701
Rat PC4        AVVVALQPHTAASDQ GTGQLSPSYHTCSAA 1                                   654
Murine PC4     QQWWWLYSHPQQPVT EGQASCHPPVTPAAA A1                                  645
Human PC4      PPRFF-NHTRLVTAG PGHTAAPALRVCSSC HASCYTCRGGSPRDC TSCPPSSTLDQQQGS    682
Murine Furin   PPGFIPQVLDTHYST ENDVEIIRASVCTPC HASCATCQGPAPTDC LSCPSHASLDPVEQT    674
Human Furin    PPGFAPQVLDTHYST ENDVETIRASVCAPC HASCATCQGPALTDC LSCPSHASLDPVEQT    674
```

Fig. 1B

```
Human PC1     EALEKLNKPSQLKDS EDSLYNDYVDVFYNT KPYKHRDDRLLQALV DILNEEN1                         753
Human PC4     CMGPTTPDSRPRLRA AACPHHRCPASAMVL SLLAVTLGGPVLCGM SMDLPLYAWLSRARA                  742
Murine Furin  CSRQSQSSRESRPQQ QPPALRPEVEMEPRL QAGL-ASHLPEVLAG LSCLIIVLIFGIVFL                  733
Human Furin   CSRQSQSSRESPPQQ QPPRLPPEVEAGQRL RAGLLPSHLPEVVAG LSCAFIVLVFVTVFL                  734

Human PC4     TPTKPQVWLPAGT                                                                   755
Murine Furin  FLHRCSGFSFRGMKV YTMDRGLISYKGLPP EAWQEECPSDSEEDE GRGERTAFIKDQSAL1                 793
Human Furin   VLQLRSGFSFRGVKV YTMDRGLISYKGLPP EAWQEECPSDSEEDE GRGERTAFIKDQSAL1                 794
```

Fig. 1C

SEQUENCE LISTING

<160> NUMBER OF SEQ ID NOS: 16

<210> SEQ ID NO 1
<211> LENGTH: 2744
<212> TYPE: DNA
<213> ORGANISM: Homo sapiens
<220> FEATURE:
<221> NAME/KEY: CDS
<222> LOCATION: (61)...(2325)

<400> SEQUENCE: 1

```
gaattcggca cgaggcggga gggaggggat ttgcgcaggc cccgctcccg ccccgcctcc      60 atg cgg ccc gcc ccg att gcg ctg tgg ctg cgc ctg gtc ttg gcc ctg     108
Met Arg Pro Ala Pro Ile Ala Leu Trp Leu Arg Leu Val Leu Ala Leu
 1               5                  10                  15 gcc ctt gtc cgc ccc cgg gct gtg ggg tgg gcc ccg gtc cga gcc ccc     156
Ala Leu Val Arg Pro Arg Ala Val Gly Trp Ala Pro Val Arg Ala Pro
             20                  25                  30 atc tat gtc agc agc tgg gcc gtc cag gtg tcc cag ggt aac cgg gag     204
Ile Tyr Val Ser Ser Trp Ala Val Gln Val Ser Gln Gly Asn Arg Glu
         35                  40                  45 gtc gag cgc ctg gca cgc aaa ttc ggc ttc gtc aac ctg ggg ccg atc     252
Val Glu Arg Leu Ala Arg Lys Phe Gly Phe Val Asn Leu Gly Pro Ile
     50                  55                  60 ttc cct gac ggg cag tac ttt cac ctg cgg cac cgg ggc gtg gtc cag     300
Phe Pro Asp Gly Gln Tyr Phe His Leu Arg His Arg Gly Val Val Gln
 65                  70                  75                  80 cag tcc ctg acc ccg cac tgg ggc cac cgc ctg cac ctg aag aaa aac     348
Gln Ser Leu Thr Pro His Trp Gly His Arg Leu His Leu Lys Lys Asn
                 85                  90                  95 ccc aag gtg cag tgg ttc cag cag cag acg ctg cag cgg cgg gtg aaa     396
Pro Lys Val Gln Trp Phe Gln Gln Gln Thr Leu Gln Arg Arg Val Lys
            100                 105                 110 cgc tct gtc gtg gtg ccc acg gac ccc tgg ttc tcc aag cag tgg tac     444
Arg Ser Val Val Val Pro Thr Asp Pro Trp Phe Ser Lys Gln Trp Tyr
        115                 120                 125 atg aac agc gag gcc caa cca gac ctg agc atc ctg cag gcc tgg agt     492
Met Asn Ser Glu Ala Gln Pro Asp Leu Ser Ile Leu Gln Ala Trp Ser
    130                 135                 140 cag ggg ctg tca ggc cag ggc atc gtg gtc tct gtg ctg gac gat ggc     540
Gln Gly Leu Ser Gly Gln Gly Ile Val Val Ser Val Leu Asp Asp Gly
145                 150                 155                 160 atc gag aag gac cac ccg gac ctc tgg gcc aac tac gac ccc ctg gcc     588
Ile Glu Lys Asp His Pro Asp Leu Trp Ala Asn Tyr Asp Pro Leu Ala
                165                 170                 175 agc tat gac ttc aat gac tac gac ccg gac ccc cag ccc cgc tac acc     636
Ser Tyr Asp Phe Asn Asp Tyr Asp Pro Asp Pro Gln Pro Arg Tyr Thr
            180                 185                 190 ccc agc aaa gag aac cgg cac ggg acc cgc tgt gct ggg gag gtg gcc     684
Pro Ser Lys Glu Asn Arg His Gly Thr Arg Cys Ala Gly Glu Val Ala
```

-continued

```
            195                 200                 205
gcg atg gcc aac aat ggc ttc tgt ggt gtg ggg gtc gct ttc aac gcc    732
Ala Met Ala Asn Asn Gly Phe Cys Gly Val Gly Val Ala Phe Asn Ala
    210                 215                 220 cga atc gga ggc gta cgg atg ctg gac ggt acc atc acc gat gtc atc    780
Arg Ile Gly Gly Val Arg Met Leu Asp Gly Thr Ile Thr Asp Val Ile
225                 230                 235                 240 gag gcc cag tcg ctg agc ctg cag ccg cag cac atc cac att tac agc    828
Glu Ala Gln Ser Leu Ser Leu Gln Pro Gln His Ile His Ile Tyr Ser
                245                 250                 255 gcc agc tgg ggt ccc gag gac gac ggc cgc acg gtg gac ggc ccc ggc    876
Ala Ser Trp Gly Pro Glu Asp Asp Gly Arg Thr Val Asp Gly Pro Gly
            260                 265                 270 atc ctc acc cgc gag gcc ttc cgg cgt ggt gtg acc aag ggc cgc ggc    924
Ile Leu Thr Arg Glu Ala Phe Arg Arg Gly Val Thr Lys Gly Arg Gly
        275                 280                 285 ggg ctg ggc acg ctc ttc atc tgg gcc tcg ggc aac ggc ggc ctg cac    972
Gly Leu Gly Thr Leu Phe Ile Trp Ala Ser Gly Asn Gly Gly Leu His
    290                 295                 300 tac gac aac tgc aac tgc gac ggc tac acc aac agc atc cac acg ctt   1020
Tyr Asp Asn Cys Asn Cys Asp Gly Tyr Thr Asn Ser Ile His Thr Leu
305                 310                 315                 320 tcc gtg ggc agc acc acc cag cag ggc cgc gtg ccc tgg tac agc gaa   1068
Ser Val Gly Ser Thr Thr Gln Gln Gly Arg Val Pro Trp Tyr Ser Glu
                325                 330                 335 gcc tgc gcc tcc acc ctc acc acc acc tac agc agc ggc gtg gcc acc   1116
Ala Cys Ala Ser Thr Leu Thr Thr Thr Tyr Ser Ser Gly Val Ala Thr
            340                 345                 350 gac ccc cag atc gtc acc acg gac ctg cat cac ggg tgc aca gac cag   1164
Asp Pro Gln Ile Val Thr Thr Asp Leu His His Gly Cys Thr Asp Gln
        355                 360                 365 cac acg ggc acc tcg gcc tca gcc cca ctg gcg gcc ggc atg atc gcc   1212
His Thr Gly Thr Ser Ala Ser Ala Pro Leu Ala Ala Gly Met Ile Ala
    370                 375                 380 cta gcg ctg gag gcc aac ccg ttc ctg acg tgg aga gac atg cag cac   1260
Leu Ala Leu Glu Ala Asn Pro Phe Leu Thr Trp Arg Asp Met Gln His
385                 390                 395                 400 ctg gtg gtc cgc gcg tcc aag ccg gcg cac ctg cag gcc gag gac tgg   1308
Leu Val Val Arg Ala Ser Lys Pro Ala His Leu Gln Ala Glu Asp Trp
                405                 410                 415 agg acc aac ggc gtg ggg cgc caa gtg agc cat cac tac gga tac ggg   1356
Arg Thr Asn Gly Val Gly Arg Gln Val Ser His His Tyr Gly Tyr Gly
            420                 425                 430 ctg ctg gac gcc ggg ctg ctg gtg gac acc gcc cgc acc tgg ctg ccc   1404
Leu Leu Asp Ala Gly Leu Leu Val Asp Thr Ala Arg Thr Trp Leu Pro
        435                 440                 445 acc cag ccg cag agg aag tgc gcc gtc cgg gtc cag agc cgc ccc acc   1452
Thr Gln Pro Gln Arg Lys Cys Ala Val Arg Val Gln Ser Arg Pro Thr
    450                 455                 460 ccc atc ctg ccg ctg atc tac atc agg gaa aac gta tcg gcc tgc gcc   1500
Pro Ile Leu Pro Leu Ile Tyr Ile Arg Glu Asn Val Ser Ala Cys Ala
465                 470                 475                 480 ggc ctc cac aac tcc atc cgc tcg ctg gag cac gtg cag gcg cag ctg   1548
Gly Leu His Asn Ser Ile Arg Ser Leu Glu His Val Gln Ala Gln Leu
                485                 490                 495 acg ctg tcc tac agc cgg cgc gga gac ctg gag atc tcg ctc acc agc   1596
Thr Leu Ser Tyr Ser Arg Arg Gly Asp Leu Glu Ile Ser Leu Thr Ser
            500                 505                 510 ccc atg ggc acg cgc tcc aca ctc gtg gcc ata cga ccc ttg gac gtc   1644
```

```
Pro Met Gly Thr Arg Ser Thr Leu Val Ala Ile Arg Pro Leu Asp Val
        515                 520                 525 agc act gaa ggc tac aac aac tgg gtc ttc atg tcc acc cac ttc tgg      1692
Ser Thr Glu Gly Tyr Asn Asn Trp Val Phe Met Ser Thr His Phe Trp
        530                 535                 540 gat gag aac cca cag ggc gtg tgg acc ctg ggc cta gag aac aag ggc      1740
Asp Glu Asn Pro Gln Gly Val Trp Thr Leu Gly Leu Glu Asn Lys Gly
545                 550                 555                 560 tac tat ttc aac acg ggg acg ttg tac cgc tac acg ctg ctc tat          1788
Tyr Tyr Phe Asn Thr Gly Thr Leu Tyr Arg Tyr Thr Leu Leu Leu Tyr
                565                 570                 575 ggg acg gcc gag gac atg aca gcg cgg cct aca ggc ccc cag gtg acc      1836
Gly Thr Ala Glu Asp Met Thr Ala Arg Pro Thr Gly Pro Gln Val Thr
            580                 585                 590 agc agc gcg tgt gtg cag cgg gac aca gag ggg ctg tgc cag gcg tgt      1884
Ser Ser Ala Cys Val Gln Arg Asp Thr Glu Gly Leu Cys Gln Ala Cys
        595                 600                 605 gac ggc ccc gcc tac atc ctg gga cag ctc tgc ctg gcc tac tgc ccc      1932
Asp Gly Pro Ala Tyr Ile Leu Gly Gln Leu Cys Leu Ala Tyr Cys Pro
        610                 615                 620 ccg cgg ttc ttc aac cac aca agg ctg gtg acc gct ggg cct ggg cac      1980
Pro Arg Phe Phe Asn His Thr Arg Leu Val Thr Ala Gly Pro Gly His
625                 630                 635                 640 acg gcg gcg ccc gcg ctg agg gtc tgc tcc agc tgc cat gcc tcc tgc      2028
Thr Ala Ala Pro Ala Leu Arg Val Cys Ser Ser Cys His Ala Ser Cys
                645                 650                 655 tac acc tgc cgc ggc ggc tcc ccg agg gac tgc acc tcc tgt ccc cca      2076
Tyr Thr Cys Arg Gly Gly Ser Pro Arg Asp Cys Thr Ser Cys Pro Pro
            660                 665                 670 tcc tcc acg ctg gac cag cag cag ggc tcc tgc atg gga ccc acc acc      2124
Ser Ser Thr Leu Asp Gln Gln Gln Gly Ser Cys Met Gly Pro Thr Thr
        675                 680                 685 ccc gac agc cgc ccc cgg ctt aga gct gcc gcc tgt ccc cac cac cgc      2172
Pro Asp Ser Arg Pro Arg Leu Arg Ala Ala Ala Cys Pro His His Arg
        690                 695                 700 tgc cca gcc tcg gcc atg gtg ctg agc ctc ctg gcc gtg acc ctc gga      2220
Cys Pro Ala Ser Ala Met Val Leu Ser Leu Leu Ala Val Thr Leu Gly
705                 710                 715                 720 ggc ccc gtc ctc tgc ggc atg tcc atg gac ctc cca cta tac gcc tgg      2268
Gly Pro Val Leu Cys Gly Met Ser Met Asp Leu Pro Leu Tyr Ala Trp
                725                 730                 735 ctc tcc cgt gcc agg gcc acc ccc acc aaa ccc cag gtc tgg ctg cca      2316
Leu Ser Arg Ala Arg Ala Thr Pro Thr Lys Pro Gln Val Trp Leu Pro
            740                 745                 750 gct gga acc tgaagttgtc agctcagaaa gcgaccttgc ccccgcctgg              2365
Ala Gly Thr
        755 gtccctgaca ggcactgctg ccatgctgcc tccccaggct ggccccagag gagcgagcac    2425 cagcacccga cgcctggcct gccagggatg ggccccgtgg aaccccgaag cctggcggga    2485 gagagagaga gagaagtctc ctctgcattt tgggtttggg cgggagtggg ctgggggag     2545 aggctggagc accccaaaag ccaggggaaa gtggagggag agaaacgtga cactgtccgc    2605 ctcgggcacc gcatccaacc tcagagtttg caaataaagg ttgcttagaa ggtgaaaaaa    2665 aaaaaaaaaa aaaaaaaaaa aaaaaaaaaa aaaaaaaaaa aaaaaaaaaa aaaaaaaaaa    2725 aaaaaaaaaa agcggccgc                                                 2744

<210> SEQ ID NO 2
```

<211> LENGTH: 755
<212> TYPE: PRT
<213> ORGANISM: Homo sapiens

<400> SEQUENCE: 2

```
Met Arg Pro Ala Pro Ile Ala Leu Trp Leu Arg Leu Val Leu Ala Leu
 1               5                  10                  15

Ala Leu Val Arg Pro Arg Ala Val Gly Trp Ala Pro Val Arg Ala Pro
            20                  25                  30

Ile Tyr Val Ser Ser Trp Ala Val Gln Val Ser Gln Gly Asn Arg Glu
        35                  40                  45

Val Glu Arg Leu Ala Arg Lys Phe Gly Phe Val Asn Leu Gly Pro Ile
    50                  55                  60

Phe Pro Asp Gly Gln Tyr Phe His Leu Arg His Arg Gly Val Val Gln
65                  70                  75                  80

Gln Ser Leu Thr Pro His Trp Gly His Arg Leu His Leu Lys Lys Asn
                85                  90                  95

Pro Lys Val Gln Trp Phe Gln Gln Gln Thr Leu Gln Arg Arg Val Lys
            100                 105                 110

Arg Ser Val Val Pro Thr Asp Pro Trp Phe Ser Lys Gln Trp Tyr
        115                 120                 125

Met Asn Ser Glu Ala Gln Pro Asp Leu Ser Ile Leu Gln Ala Trp Ser
    130                 135                 140

Gln Gly Leu Ser Gly Gln Gly Ile Val Val Ser Val Leu Asp Asp Gly
145                 150                 155                 160

Ile Glu Lys Asp His Pro Asp Leu Trp Ala Asn Tyr Asp Pro Leu Ala
                165                 170                 175

Ser Tyr Asp Phe Asn Asp Tyr Asp Pro Asp Pro Gln Pro Arg Tyr Thr
            180                 185                 190

Pro Ser Lys Glu Asn Arg His Gly Thr Arg Cys Ala Gly Glu Val Ala
        195                 200                 205

Ala Met Ala Asn Asn Gly Phe Cys Gly Val Gly Val Ala Phe Asn Ala
    210                 215                 220

Arg Ile Gly Gly Val Arg Met Leu Asp Gly Thr Ile Thr Asp Val Ile
225                 230                 235                 240

Glu Ala Gln Ser Leu Ser Leu Gln Pro Gln His Ile His Ile Tyr Ser
                245                 250                 255

Ala Ser Trp Gly Pro Glu Asp Asp Gly Arg Thr Val Asp Gly Pro Gly
            260                 265                 270

Ile Leu Thr Arg Glu Ala Phe Arg Arg Gly Val Thr Lys Gly Arg Gly
        275                 280                 285

Gly Leu Gly Thr Leu Phe Ile Trp Ala Ser Gly Asn Gly Gly Leu His
    290                 295                 300

Tyr Asp Asn Cys Asn Cys Asp Gly Tyr Thr Asn Ser Ile His Thr Leu
305                 310                 315                 320

Ser Val Gly Ser Thr Thr Gln Gln Gly Arg Val Pro Trp Tyr Ser Glu
                325                 330                 335

Ala Cys Ala Ser Thr Leu Thr Thr Thr Tyr Ser Ser Gly Val Ala Thr
            340                 345                 350

Asp Pro Gln Ile Val Thr Thr Asp Leu His His Gly Cys Thr Asp Gln
        355                 360                 365

His Thr Gly Thr Ser Ala Ser Ala Pro Leu Ala Ala Gly Met Ile Ala
    370                 375                 380

Leu Ala Leu Glu Ala Asn Pro Phe Leu Thr Trp Arg Asp Met Gln His
```

```
                385                 390                 395                 400
Leu Val Val Arg Ala Ser Lys Pro Ala His Leu Gln Ala Glu Asp Trp
                405                 410                 415
Arg Thr Asn Gly Val Gly Arg Gln Val Ser His His Tyr Gly Tyr Gly
                420                 425                 430
Leu Leu Asp Ala Gly Leu Leu Val Asp Thr Ala Arg Thr Trp Leu Pro
                435                 440                 445
Thr Gln Pro Gln Arg Lys Cys Ala Val Arg Val Gln Ser Arg Pro Thr
                450                 455                 460
Pro Ile Leu Pro Leu Ile Tyr Ile Arg Glu Asn Val Ser Ala Cys Ala
465                 470                 475                 480
Gly Leu His Asn Ser Ile Arg Ser Leu Glu His Val Gln Ala Gln Leu
                485                 490                 495
Thr Leu Ser Tyr Ser Arg Arg Gly Asp Leu Glu Ile Ser Leu Thr Ser
                500                 505                 510
Pro Met Gly Thr Arg Ser Thr Leu Val Ala Ile Arg Pro Leu Asp Val
                515                 520                 525
Ser Thr Glu Gly Tyr Asn Asn Trp Val Phe Met Ser Thr His Phe Trp
                530                 535                 540
Asp Glu Asn Pro Gln Gly Val Trp Thr Leu Gly Leu Glu Asn Lys Gly
545                 550                 555                 560
Tyr Tyr Phe Asn Thr Gly Thr Leu Tyr Arg Tyr Thr Leu Leu Leu Tyr
                565                 570                 575
Gly Thr Ala Glu Asp Met Thr Ala Arg Pro Thr Gly Pro Gln Val Thr
                580                 585                 590
Ser Ser Ala Cys Val Gln Arg Asp Thr Glu Gly Leu Cys Gln Ala Cys
                595                 600                 605
Asp Gly Pro Ala Tyr Ile Leu Gly Gln Leu Cys Leu Ala Tyr Cys Pro
                610                 615                 620
Pro Arg Phe Phe Asn His Thr Arg Leu Val Thr Ala Gly Pro Gly His
625                 630                 635                 640
Thr Ala Ala Pro Ala Leu Arg Val Cys Ser Ser Cys His Ala Ser Cys
                645                 650                 655
Tyr Thr Cys Arg Gly Gly Ser Pro Arg Asp Cys Thr Ser Cys Pro Pro
                660                 665                 670
Ser Ser Thr Leu Asp Gln Gln Gln Gly Ser Cys Met Gly Pro Thr Thr
                675                 680                 685
Pro Asp Ser Arg Pro Arg Leu Arg Ala Ala Ala Cys Pro His His Arg
                690                 695                 700
Cys Pro Ala Ser Ala Met Val Leu Ser Leu Leu Ala Val Thr Leu Gly
705                 710                 715                 720
Gly Pro Val Leu Cys Gly Met Ser Met Asp Leu Pro Leu Tyr Ala Trp
                725                 730                 735
Leu Ser Arg Ala Arg Ala Thr Pro Thr Lys Pro Gln Val Trp Leu Pro
                740                 745                 750
Ala Gly Thr
        755

<210> SEQ ID NO 3
<211> LENGTH: 2265
<212> TYPE: DNA
<213> ORGANISM: Artificial Sequence
<220> FEATURE:
<223> OTHER INFORMATION: Degenerate polynucleotide sequence for human
      prohormone convertase 4
```

-continued

<220> FEATURE:
<221> NAME/KEY: misc_feature
<222> LOCATION: (1)...(2265)
<223> OTHER INFORMATION: n = A,T,C or G

<400> SEQUENCE: 3

```
atgmgnccng cnccnathgc nytntggytn mgnytngtny tngcnytngc nytngtnmgn     60
ccnmgngcng tnggntgggc nccngtnmgn gcnccnatht aygtnwsnws ntgggcngtn    120
cargtnwsnc arggnaaymg ngargtngar mgnytngcnm gnaarttygg nttygtnaay    180
ytnggnccna thttyccnga yggncartay ttycayytnm gncaymgngg ngtngtncar    240
carwsnytna cnccncaytg gggncaymgn ytncayytna araaraaycc naargtncar    300
tggttycarc arcaracnyt ncarmgnmgn gtnaarmgnw sngtngtngt nccnacngay    360
ccntggttyw snaarcartg gtayatgaay wsngargcnc arccngayyt nwsnathytn    420
cargcntggw sncarggnyt nwsnggncar ggnathgtng tnwsngtnyt ngaygayggn    480
athgaraarg aycayccnga yytntgggcn aaytaygayc cnytngcnws ntaygaytty    540
aaygaytayg ayccngaycc ncarccnmgn tayacnccnw snaargaraa ymgncayggn    600
acnmgntgyg cnggngargt ngcngcnatg gcnaayaayg gnttytgygg ngtnggngtn    660
gcnttyaayg cnmgnathgg nggngtnmgn atgytngayg gnacnathac ngaygtnath    720
gargcncarw snytnwsnyt ncarccncar cayathcaya thtaywsngc nwsntggggn    780
ccngargayg ayggnmgnac ngtngayggn ccnggnathy tnacnmgnga rgcnttymgn    840
mgnggngtna cnaarggnmg nggnggnytn ggnacnytnt tyathtgggc nwsnggnaay    900
ggnggnytnc aytaygayaa ytgyaaytgy gayggntaya cnaaywsnat hcayacnytn    960
wsngtnggnw snacnacnca rcarggnmgn gtnccntggt aywsngargc ntgygcnwsn   1020
acnytnacna cnacntayws nwsnggngtn gcnacngayc cncarathgt nacnacngay   1080
ytncaycayg gntgyacnga ycarcayacn ggnacnwsng cnwsngcncc nytngcngcn   1140
ggnatgathg cnytngcnyt ngargcnaay ccnttyytna cntggmgnga yatgcarcay   1200
ytngtngtnm gngcnwsnaa rccngcncay ytncargcng argaytggmg nacnaayggn   1260
gtnggnmgnc argtnwsnca ycaytayggn tayggnytny tngaygcngg nytnytngtn   1320
gayacngcnm gnacntggyt nccnacncar ccncarmgna artgygcngt nmgngtncar   1380
wsnmgnccna cnccnathyt nccnytnath tayathmgng araaygtnws ngcntgygcn   1440
ggnytncaya aywsnathmg nwsnytngar caygtncarg cncarytnac nytnwsntay   1500
wsnmgnmgng gngayytnga rathwsnytn acnwsnccna tgggnacnmg nwsnacnytn   1560
gtngcnathm gnccnytnga ygtnwsnacn garggntaya ayaaytgggt nttyatgwsn   1620
acncayttyt gggaygaraa yccncarggn gtntggacny tnggnytnga raayaarggn   1680
taytayttya ayacnggnac nytntaymgn tayacnytny tnytntaygg nacngcngar   1740
gayatgacng cnmgnccnac nggnccncar gtnacnwsnw sngcntgygt ncarmgngay   1800
acngarggny tntgycargc ntgygayggn ccngcntaya thytnggnca rytntgyytn   1860
gcntaytgyc cnccnmgntt yttyaaycay acnmgnytng tnacngcngg nccnggncay   1920
acngcngcnc cngcnytnmg ngtntgywsn wsntgycayg cnwsntgyta yacntgymgn   1980
ggnggnwsnc cnmgngaytg yacnwsntgy ccnccnwsnw snacnytnga ycarcarcar   2040
ggnwsntgya tgggnccnac nacnccngay wsnmgnccnm gnytnmgngc ngcngcntgy   2100
ccncaycaym gntgyccngc nwsngcnatg gtnytnwsny tnytngcngt nacnytnggn   2160
```

```
ggnccngtny tntgyggnat gwsnatggay ytnccnytnt aygcntggyt nwsnmgngcn    2220
mgngcnacnc cnacnaarcc ncargtntgg ytnccngcng gnacn                   2265

<210> SEQ ID NO 4
<211> LENGTH: 5
<212> TYPE: PRT
<213> ORGANISM: Homo sapiens

<400> SEQUENCE: 4

Arg Arg Val Lys Arg
 1               5

<210> SEQ ID NO 5
<211> LENGTH: 49
<212> TYPE: DNA
<213> ORGANISM: Artificial Sequence
<220> FEATURE:
<223> OTHER INFORMATION: Oligonucleotide primer ZC6091

<400> SEQUENCE: 5
gagcacagaa ttcactactc gaggcggccg cttttttttt tttttttt                49

<210> SEQ ID NO 6
<211> LENGTH: 2458
<212> TYPE: DNA
<213> ORGANISM: Rattus norvegicus

<400> SEQUENCE: 6
atgcggccct cccagacagc gctgtggctg gtctggtttt tgtctttggc cctcctggct    60
gtggggtggg cctcagcccg accacccatc tatgtcagca gctgggcagt gcgggtgacc   120
aaaggttacc aggaggctga gcgcctggca cgtaaatttg gcttcgtcaa cctgggacag   180
atctttcctg atgaccagta tttccatctg aggcaccggg gtgtggccca gcagtccctg   240
actccgcact ggggccaccg tctgcgcctg aagaaagagc ccaaggtgcg gtggtttgag   300
cagcagactt tgaggcggcg ggtgaagcgc tccctggtgg tacccacaga cccctggttt   360
tccaagcagt ggtacatgaa caaggagata gaacaagatc tcaacatcct aaaggtttgg   420
aaccagggac tgactggccg gggagtggtg gtctccatct ggatgatgg cattgagaag   480 gaccatccgg acctctgggc taattatgac cccctggcca gctatgactt caatgattac   540
gacccagatc cccagcctcg atacacaccc aacgatgaga accggcatgg aacacgctgc   600
gctggggagg tgtctgccac agcaaacaac ggtttctgtg gtgccggtgt ggccttcaat   660
gccagaattg gaggcgtgcg catgttggat ggagccatca ctgacatcgt ggaggctcag   720
tccctcagcc tgcagccgca acacatacac atctatagcg ccagttgggg ccccgaggat   780
gatgggcgca cagtggacgg acccggcctc ctcacgcagg aggccttcag gcgtggtgta   840
accaagggcc gccaagggct gggcacgctg ttcatctggg cctcgggaaa cggtggcctc   900
cactacgaca actgcaattg tgacggctac accaacagca tccacacgct gtcagtgggc   960
agtaccacgc ggcagggccg agtgccctgg tacagcgagg cctgcgcctc cacgttcacc  1020
accaccttca gcagcggtgt ggtcaccgac ccacagatcg tcaccacgga cctacaccat  1080
caatgcaccg acaagcacac gggcacctcg gcctccgccc cgctggccgc tgcatgatc   1140 gccctggcgc tggaggccaa cccgctgctg acctggaggg acctgcagca cctggtggtc  1200
cgcgcgtcca ggccggcgca gctgcaggcg gaggactgga ggatcaacgg cgtggggcgc  1260
caagtgagcc accactatgg ctatgggctg ctggacgcgg ggctgctggt agacctggct  1320
```

```
cgcgtgtggc tccctactaa gcctcagaag aaatgcacca ttcgggtggt gcacacccca    1380
acccccatcc tgcctcggat gctggtgcca agaacgtga ctgtatgctg cgatggctcg    1440
cgccgccgcc tcatccgctc gctagagcat gttcaggtcc agctgtcgct ctcctacagc    1500
cgccgcgggg acctggagat cttcctcacc agccccatgg gcacgcgctc cacgcttgtg    1560
gccatcagac ccttggatat cagcggccaa ggctacaaca actggatctt catgtctact    1620
cactactggg atgaggaccc gcagggcctg tggaccctgg ggctggagaa taagggctac    1680
tattataaca caggaactct gtactactgc acgctgctgc tgtatgggac ggcagaggac    1740
atgacagcgc ggccccagac ccccaggtg accagctgcg cgcacgcatg tgcagaggga    1800
cacagagggg ctgtgccagg aaagtcattg tccctctcc attgtggcag aactctgcct    1860
catctccagc aagcagtggt ggtggctcta cagccacaca cagcagccag tgaccaaggg    1920
acaggacagc tgtcaccctc ctaccacacc tgctcggcag cttgaccagc gactacactg    1980
cctgttccct gcccctcatg ctgggagtgc ttcagagccc ctccaaggct tgtcacctct    2040
ggcagccatc ctggctatca gtcttgggcc atggtgctgt ccctgctaac cagggccttt    2100
ggaaggcccc tcatcttgag gaaggccac ctctccccag gctggatacc cctggggagc    2160
cagagatgcc ccactctcag gacagaaggc cggtacccca aggccctgct cccaggccgg    2220
gataggaata tgcccagaa ggccacggca gagagctgca tgggtcacgt gacagcccgc    2280
agctcagcct cagctgctcc cagtggaaga gacgtttcct cattcttttt ggagcaggta    2340
tggcagacaa gaggtcagac cacagccacc aaccacctgc cccttccctg tctccaaacc    2400
atccccatgt ctaacctcat agttggcaaa taagttaaa cagaaaaaaa aaaaaaaa    2458
```

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer ZC11,808

<400> SEQUENCE: 7
tggctgggtc tggttttgtc tttgg                                        25

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide primer ZC11,809

<400> SEQUENCE: 8
gcattgatgg tgtaggtccg tggt                                         24

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide primer ZC11,870

<400> SEQUENCE: 9
tttggccctc ctggctgtgg ggtg                                         24

<210> SEQ ID NO 10
<211> LENGTH: 24
<212> TYPE: DNA
<213> ORGANISM: Artificial Sequence

```
<220> FEATURE:
<223> OTHER INFORMATION: Oligonucleotide primer ZC11,871

<400> SEQUENCE: 10
tgctgaaggt ggtggtgaac gtgg                                           24

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide primer ZC13,557

<400> SEQUENCE: 11
cagccgcagc acatccacat ttacag                                         26

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer ZC13,558

<400> SEQUENCE: 12
gggtgaggat gccggggccg t                                              21

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer ZC13,359

<400> SEQUENCE: 13
tacgaccctt ggacgtcagc a                                              21

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide primer ZC13,358

<400> SEQUENCE: 14
ggatctagat caggttccag ctggcagcca                                     30

<210> SEQ ID NO 15
<211> LENGTH: 19
<212> TYPE: DNA
<213> ORGANISM: Artificial Sequence
<220> FEATURE:
<223> OTHER INFORMATION: Oligonucleotide primer ZC12,634

<400> SEQUENCE: 15
gagccatcac tacggatac                                                 19

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide primer ZC12,945

<400> SEQUENCE: 16
gctgtcccag gatgtaggc                                                 19
```

HUMAN PROHORMONE CONVERTASE 4

The present application is a divisional application of co-pending U.S. patent application Ser. No. 09/071,101 filed May 1, 1998 (now U.S. Pat. No. 6,013,503) which is related to Provisional Application 60/044,015 filed on May 6, 1997. Under 35 U.S.C. § 119(e)(1), this application claims benefit of said Provisional Application.

BACKGROUND OF THE INVENTION

Many proteins and hormones, synthesized as precursors, are processed into their mature forms by highly-specific proteolytic enzymes of the prohormone convertase family. This family of mammalian endoproteases carries out intracellular cleavage at the COOH-terminal side of dibasic sites within their substrate polypeptides. Members of this prohormone convertase (PC) family are $Ca^{++}$-dependent serine proteases related to the yeast dibasic-specific endoprotease Kex2 (Smeekins, S.P., *Bio/Technology* 11: 182–186, 1993). Moreover, the catalytic domains thereof are organized similarly to bacterial subtilisins. At least six mammalian prohormone convertases have been found including PC2, PC3/PC1, PC4, PC5/6 furin/PACE and PACE4 (Smeekins, S.P., ibid., Seidah, N.G. et al., *Biochimie* (France) 76: 197–209, 1994).

Mammalian prohormone convertases act on a wide variety of precursor molecules having an array of biological activities. The proinsulin prohormone was the first substrate precursor identified. Subsequently, over 150 substrates have been found in organisms from yeast to mammals; including neuropeptides, peptide hormones, growth factors and their receptors, plasma and coagulation proteins, retroviral envelope proteins and cellular toxins, e.g., anthrax. Cleavage sites include basic amino acids, with cleavage occurring at paired basic residues, usually after Lys-Arg or Arg-Arg and more rarely Arg-Lys or Lys-Lys (Smeekins, S.P., ibid.).

The prohormone convertase family exhibits tissue-specific expression and cellular compartmentalization, which may relate to biological function. For example, PC1/3 and PC2 are solely expressed in neuroendocrine tissues. Biological activities of these proteins are localized to the regulated secretory pathway in neuroendocrine cells, specifically in secretory granules; and both play important roles in processing precursors in the granules such as proglucagon, proopiomelanocortin (POMC) and proinsulin. Thus, intracellular localization and tissue specificity appear to reflect where the biological activities of these endoproteases are manifested.

PC4 exhibits highly specific tissue-selectivity of gene expression. PC4 has been isolated from mice and rats and is solely expressed in the testis. In mice, PC4 gene expression occurs around the 20th day of gestation corresponding with the first stages of spermatogenesis. High PC4 mRNA expression levels are found in germ cells but not in Leydig, Sertoli, or peritubular cells. In situ hybridization demonstrates mRNA expression in the pachytene spermatocytes and the round spermatids, but not in elongating spermatids (N.G. Seidah et al., *Mol. Endocrinol.* 6: 1559–1570, 1992). Moreover, in both rat and mouse, three PC4 mRNAs are observed; these RNAs are probably derived from differential splicing and/or exon skipping events. The biological function of murine and rat PC4 proteins derived from the principle or alternatively spliced forms is unknown.

Spermatogenesis is a sequential process taking place in the seminiferous tubules, where germ (or sperm) cells ultimately mature into spermatozoa. Peptides produced within the testis are potential paracrine and autocrine factors mediating interactions between testicular cells. Most of these known potential peptide substrates are produced within Leydig and Sertoli cells which are non-germ cells. Sertoli cells, located within the seminiferous tubules, are in contact with the germ cells and may directly produce testis-specific factors that influence germ cell maturation. Other factors that influence germ cells may be paracrine or endocrine factors; many of these molecules produced outside the seminiferous tubules are transported into the germ cell microenvironment by transport and binding proteins expressed by the Sertoli cells. In addition, paracrine factors that cross the cellular barrier and enter the sperm cell microenvironment include molecules secreted from Leydig cells. Leydig cells are located in the interstitial space found between the seminiferous tubules, and produce several factors that may play important roles in the maturation process, such as testosterone, Leydig factor, IGF-1, inhibin and prohibin. These and other factors may act specifically during a defined stage in the spermatogenic cycle. Moreover, some peptide hormones expressed in germ cells, located in close proximity to Sertoli cells, are potential paracrine and autocrine factors that mediate interactions between testicular cells. For example, the opioid peptides, POMC and proenkephalin, are expressed and presumably processed in germ cells. Interestingly, murine proenkephalin has a similar mRNA expression profile to murine PC4 during spermatogenesis (S. Torii, et al., *FEBS Let.* 316: 12–16, 1993). The stage-specific expression of murine PC4 implicates a biological role in processing prohormone factors from the testis. Although a role for PC4 in spermatogenesis is suggested, the function of PC4 is unknown.

Thus, the human homologue is sought. The present invention advantageously provides the isolation of a human homologue to murine PC4.

SUMMARY OF THE INVENTION

The present invention provides an isolated polynucleotide encoding a human prohormone convertase 4 polypeptide comprising a sequence of amino acid residues that is at least 90% identical to an amino acid sequence selected from the group consisting of: (a) the amino acid sequence as shown in SEQ ID NO:2 from amino acid number 114 (Ser) to amino acid number 443 (Ala); (b) the amino acid sequence as shown in SEQ ID NO:2 from amino acid number 114 (Ser) to amino acid number 755 (Thr); (c) the amino acid sequence as shown in SEQ ID NO:2 from amino acid number 20 (Arg) to amino acid number 755 (Thr); and (d) the amino acid sequence as shown in SEQ ID NO:2 from amino acid number 1 (Met) to amino acid number 755 (Thr) Within another embodiment, the isolated human prohormone convertase 4 polynucleotide disclosed above is selected from the group consisting of: (a) a polynucleotide sequence as shown in SEQ ID NO:1 from nucleotide 400 to nucleotide 1389; (b) a polynucleotide sequence as shown in SEQ ID NO:1 from nucleotide 400 to nucleotide 2325; (c) a polynucleotide sequence as shown in SEQ ID NO:1 from nucleotide 118 to nucleotide 2325; and (d) a polynucleotide sequence as shown in SEQ ID NO:1 from nucleotide 61 to nucleotide 2325. Within another embodiment, the isolated human prohormone convertase 4 polynucleotide disclosed above comprises nucleotide 1 to nucleotide 2265 of SEQ ID NO:3. Within another embodiment, the isolated human prohormone convertase 4 polynucleotide disclosed above encodes a human prohormone convertase 4 polypeptide consisting essentially of a sequence of amino acid residues that is at least 90% identical to an amino acid sequence as shown in SEQ ID NO:2 from amino acid number 20 (Arg) to amino acid number 755 (Thr). Within another embodiment, the isolated polynucleotide disclosed above encodes a human prohormone convertase 4 polypeptide consisting essentially of a sequence of amino acid residues as shown in SEQ ID NO:2 from amino acid number 20 (Arg) to amino acid number 755 (Thr).

Within a second aspect, the present invention provides an expression vector comprising the following operably linked elements: a transcription promoter; a DNA segment encoding a prohormone convertase polypeptide that is at least 90% identical to an amino acid sequence as shown in SEQ ID NO:2 from amino acid number 20 (Arg) to amino acid number 755 (Thr); and a transcription terminator. Within another embodiment, the expression vector disclosed above further comprises a secretory signal sequence operably linked to the DNA segment.

Within a third aspect, the present invention provides a cultured cell into which has been introduced an expression vector as disclosed above, wherein the cell expresses a polypeptide encoded by the DNA segment.

Within another aspect, the present invention provides a DNA construct encoding a fusion protein, the DNA construct comprising: a first DNA segment encoding a polypeptide that is at least 90% identical to a sequence of amino acid residues selected from the group consisting of: (a) the amino acid sequence of SEQ ID NO: 2 from residue number 1 (Met), to residue number 21 (Pro); (b) the amino acid sequence of SEQ ID NO: 2 from residue number 20 (Arg), to residue number 113 (Arg); (c) the amino acid sequence of SEQ ID NO: 2 from residue number 114 (Ser), to residue number 443 (Ala); (d) the amino acid sequence of SEQ ID NO: 2 from residue number 444 (Arg), to residue number 561 (Tyr); (e) the amino acid sequence of SEQ ID NO: 2 from residue number 562 (Tyr), to residue number 755 (Thr); (f) the amino acid sequence of SEQ ID NO: 2 from residue number 114 (Ser), to residue number 755 (Thr); (g) the amino acid sequence of SEQ ID NO: 2 from residue number 20 (Arg), to residue number 755 (Thr); and at least one other DNA segment encoding an additional polypeptide, wherein the first and other DNA segments are connected in-frame; and encode the fusion protein. Within another embodiment, the present invention provides a fusion protein produced by a method comprising: culturing a host cell into which has been introduced a vector comprising the following operably linked elements: (a) a transcriptional promoter; (b) a DNA construct encoding a fusion protein as disclosed above; and (c) a transcriptional terminator; and recovering the protein encoded by the DNA segment.

Within another aspect, the present invention provides an isolated polypeptide comprising a sequence of amino acid residues that is at least 90% identical to an amino acid sequence selected from the group consisting of: (a) the amino acid sequence as shown in SEQ ID NO:2 from amino acid number 114 (Ser) to amino acid number 443 (Ala); (b) the amino acid sequence as shown in SEQ ID NO:2 from amino acid number 114 (Ser) to amino acid number 755 (Thr); (c) the amino acid sequence as shown in SEQ ID NO:2 from amino acid number 20 (Arg) to amino acid number 755 (Thr); and (d) the amino acid sequence as shown in SEQ ID NO:2 from amino acid number 1 (Met) to amino acid number 755 (Thr). Within another embodiment, the isolated polypeptide disclosed above consists essentially of a sequence of amino acid residues that is at least 90% identical to an amino acid sequence as shown in SEQ ID NO:2 from amino acid number 20 (Arg) to amino acid number 755 (Thr). Within another embodiment, the isolated polypeptide disclosed above, is as shown in SEQ ID NO:2 from amino acid number 20 (Arg) to amino acid number 755 (Thr).

Within another aspect, the present invention provides a method of producing a human prohormone convertase 4 polypeptide comprising: culturing a cell as disclosed above; and isolating the human prohormone convertase polypeptide produced by the cell.

Within another aspect, the present invention provides a method of determining polypeptide prohormone substrates of a human prohormone convertase 4 polypeptide comprising: culturing a cell into which has been introduced an expression vector as disclosed above, wherein the cell expresses a human prohormone convertase polypeptide encoded by the DNA segment and co-expresses a test substrate prohormone polypeptide; and detecting cleavage products resulting from cleavage of the test substrate by the human prohormone convertase 4. Within another embodiment, the method of determining polypeptide prohormone substrates of a human prohormone convertase 4 polypeptide comprises: combining in vitro, prohormone convertase 4 polypeptide according to claim 11 with a test substrate polypeptide; and detecting cleavage products resulting from cleavage of the test substrate by the human prohormone convertase 4 polypeptide.

Within another aspect, the present invention provides a method of detecting, in a test sample, the presence of a modulator of human prohormone convertase polypeptide activity, comprising: culturing a cell into which has been introduced an expression vector as disclosed above, wherein the cell expresses the human prohormone convertase polypeptide encoded by the DNA segment and co-expresses a known indicator prohormone polypeptide substrate, in the presence and absence of a test sample; and comparing levels of cleavage products resulting from cleavage of the substrate by the human prohormone convertase polypeptide, in the presence and absence of the test sample, by a biological or biochemical assay; and determining from the comparison, the presence of the modulator of human prohormone convertase polypeptide activity in the test sample.

Within another aspect, the present invention provides a method of producing an antibody to human prohormone convertase 4 polypeptide comprising: inoculating an animal with a polypeptide selected from the group consisting of: (a) a polypeptide consisting of 9 to 755 amino acids, wherein the polypeptide is at least 90% identical to a contiguous stretch of amino acids in SEQ ID NO:2 from amino acid number 20 (Arg) to amino acid number 755 (Ser); (b) a polypeptide as disclosed above; (c) a polypeptide with an amino acid sequence that is at least 90% identical to residue number 444 (Arg), to residue number 561 (Tyr) of SEQ ID NO:2; and (d) a polypeptide with an amino acid sequence that is at least 90% identical to residue number 562 (Tyr), to residue number 755 (Thr) of SEQ ID NO:2, wherein the polypeptide elicits an immune response in the animal; and isolating the antibody from the animal. Within another embodiment the antibody produced by the method disclosed above binds to a human prohormone convertase 4 polypeptide. Within another embodiment, the antibody disclosed above is a monoclonal antibody.

Within another aspect, the present invention provides an antibody which specifically binds to a polypeptide as disclosed above.

These and other aspects of the invention will become evident upon reference to the following detailed description of the invention and attached drawing.

BRIEF DESCRIPTION OF THE DRAWINGS

The FIGURE is a multiple alignment of human PC1, human PC2, rat PC4, murine PC4, a novel human PC4 of the present invention, murine furin, and human furin.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–1210, 1988; available from Eastman Kodak Co., New Haven, Conn.), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "cleavage products" is used to denote prohormone polypeptide fragments resulting from cleavage of the unprocessed prohormone polypeptide by a prohormone convertase.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of <$10^9$ $M^{-1}$.

The term "complement of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide) Degenerate codons contain different triplets of nucleotides, but generally encode the same amino acid residue (i.e., GAU and GAC triplets each encode Asp).

A "DNA construct" is a single or double stranded, linear or circular DNA molecule that comprises segments of DNA combined and juxtaposed in a manner not found in nature. DNA constructs exist as a result of human manipulation, and include clones and other copies of manipulated molecules.

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators, and the like. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e., greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway. A secretory signal sequence will direct a polypeptide into the secretory pathway of a cell but may or may not target a polypeptide containing the sequence to be actually secreted from the cell.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

Teachings of all references cited herein are in their entirety incorporated by reference.

The present invention is based in part upon the discovery of a novel DNA sequence that encodes a protein with homology to the prohormone convertase family (e.g., murine and rat PC4, PC2, PC1, furin). The DNA sequence was designated human prohormone convertase 4, abbreviated herein as "human PC4." Analysis of the tissue distribution of the mRNA corresponding to this novel cDNA showed that mRNA expression was restricted to the testis. Such tissue-specific expression indicates a role as a prohormone convertase that fully or partially processes the prohormone polypeptides of growth or differentiation factors to mature or active forms for testis-specific and non-testis cell types.

Mammalian prohormone convertases share common structural features. See, Smeekins, S.P., ibid., and Seidah, N. *Methods in Enz.*, 244: 175–188, 1995, for review. All contain an N-terminal secretory peptide that directs the protein into the secretory pathway. This region is followed by the Homo-A domain, likely involved in protease folding. Removal of the Homo-A domain by autocatalysis is essential for proteolytic activation. Following the Homo-A domain is the catalytic domain, which is essential for activity. The catalytic domain has the highest amino acid sequence identity with the bacterial subtilisin catalytic region. Adjacent to the catalytic domain is the Homo-B domain, which is also essential for enzymatic activity. Beyond this region, at the C-terminal end, prohormone convertases structurally diverge. The functional role for the C-terminal regions is unknown but is likely involved in cell and organelle-specific targeting of mammalian prohormone convertases.

The present invention provides for a novel human prohormone convertase. Analysis of a human cDNA encoding a prohormone convertase (SEQ ID NO: 1) revealed an open reading frame encoding 755 amino acids (SEQ ID NO: 2), comprising a putative secretory peptide (see, SEQ ID NO: 2 from residue 1 (Met) to residue 19 (Val)) and a mature polypeptide (see, SEQ ID NO:2 from residue 20 (Arg) to residue 755 (Thr)). As shown in the Figure, the mature polypeptide has homology with other members of the Kex2 family of endoproteases, which includes rat and murine PC4, human furin, human PC1 and human PC2. As described above, this protein family is characterized by a conserved subtilisin-like catalytic domain (see, SEQ ID NO: 2 from residue 114 (Ser) to residue 443 (Ala) ) which is flanked at the $NH_2$- and COOH-terminal ends by regions that are less conserved, referred to as Homo-A (see, SEQ ID NO: 2 from residue 20 (Arg) to residue 113 (Arg)) and Homo-B (see, SEQ ID NO: 2 from residue 444 (Arg) to residue 561 (Tyr)) domains respectively (Nakayama et al.,*J. Biochem* (Tokyo), 109: 803–806, 1991). The active site Asp, His, and Ser residues and catalytically important Asn residue present in rat and murine PC4 are conserved in the human PC4 (see, SEQ ID NO: 2, residues Asp-158, His-198, Ser-372 and Asn-300). The site of signal peptidase cleavage is predicted to occur after residue 19 (Val), based on alignment of the human prohormone convertases. The conserved Arg-Gly-Asp sequence (see, SEQ ID NO: 2, residues number 503 to number 505), found in all known mammalian prohormone convertases, is present in human PC4 (Nakayama, ibid., and references therein). Human PC4 is predicted to be synthesized as a precursor enzyme (zymogen) which undergoes autocatalytic cleavage at the C-terminal side of an Arg-Arg-Val-Lys-Arg (SEQ ID NO:4; see also, SEQ ID NO: 2 from residue number 109 (Arg) to residue number 113 (Arg)) sequence to yield an active enzyme. A similar zymogen activation sequence is observed for Kex2 and rat PC4 (Nakayama et al., *J. Biochem* (Tokyo), 109: 803–806, 1991). The C-terminal domain (see, SEQ ID NO: 2 from residue 562 (Tyr) to residue 755 (Thr)) unique to human PC4 has the highest sequence identity to furin. The function of this domain may be involved in cell and organelle-specific targeting.

The highly conserved amino acids in, for example, the subtilisin-like catalytic domain of human PC4, can be used as a tool to identify new family members. For instance, reverse transcription-polymerase chain reaction (RT-PCR) can be used to amplify sequences encoding the conserved subtilisin-like catalytic domain from RNA obtained from a variety of tissue sources or cell lines. In particular, highly degenerate primers designed from the human PC4 sequences are useful for this purpose.

The present invention also provides polynucleotide molecules, including DNA and RNA molecules, that encode the human PC4 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the human PC4 polypeptide of SEQ ID NO:2. Those skilled in the art will recognize that the degenerate sequence of SEQ ID NO:3 also provides all RNA sequences encoding SEQ ID NO:2 by substituting U for T. Thus, human PC4 polypeptide-encoding polynucleotides comprising nucleotide 1 to nucleotide 2265 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |

TABLE 2-continued

| Amino Acid | One Letter Code | Codons | Degenerate Codon |
|---|---|---|---|
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the NaCl concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of human PC4 RNA. Such tissues and cells are identified by Northern blotting (Thomas, *Proc. Natl. Acad. Sci. USA* 77:5201, 1980), and include testis tissue, and testis-derived cell lines. Total RNA can be prepared using guanidine HCl extraction followed by isolation by centrifugation in a CsCl gradient (Chirgwin et al., *Biochemistry* 18:52–94, 1979). Poly(A)$^+$ RNA is prepared from total RNA using the method of Aviv and Leder (*Proc. Natl. Acad. Sci. USA* 69:1408–12, 1972). Complementary DNA (CDNA) is prepared from poly(A)$^+$ RNA using known methods. In the alternative, genomic DNA can be isolated. Polynucleotides encoding human PC4 polypeptides are then identified and isolated by, for example, hybridization or PCR.

A full-length clone encoding human PC4 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to human PC4, receptor fragments, or other specific binding partners. The present invention also provides for the isolation of human genomic sequences encoding a human prohormone convertase 4. Probes derived from SEQ ID NO: 1 can be used to screen genomic libraries from human sources to clone human genomic sequences of human PC4 according to standard procedures known in the art, and disclosed herein.

Those skilled in the art will recognize that the sequence disclosed in SEQ ID NO:1 represents a single allele of human PC4 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. The present invention also provides for MRNA splice variant forms of the isolated polynucleotides that may occur naturally as a result of gene expression of human prohormone convertase 4. cDNAs generated from alternatively spliced mRNAs, which retain the properties of the human PC4 polypeptide are included within the scope of the present invention, as are polypeptides encoded by such cDNAs and mRNAs. Splice variants of this sequence can be cloned by probing human cDNA libraries, e.g. a human testicular cDNA library, according to standard procedures.

The present invention also provides isolated human prohormone convertase 4 polypeptides that are substantially homologous to the polypeptides of SEQ ID NO: 2 and their orthologs. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having at least 85%, sequence identity to the sequences shown in SEQ ID NO: 2 or splice variants of SEQ ID NO:2. Such polypeptides will more preferably be at least 90% identical, and most preferably 95% or more identical to SEQ ID NO: 2 or splice variants of SEQ ID NO:2. Percent sequence identity is determined by conventional methods. see, for example, Altschul et al., Bull. Math. Bio. 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |

TABLE 3-continued

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

The percent identity of the optimal alignment is calculated as:

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Variant human PC4 polypeptides or substantially homologous human PC4 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag, such as a small extension that facilitates purification, such as a poly-histidine tract, an antigenic epitope or a binding domain. See, in general Ford et al., Protein Expression and Purification 2: 95–107, 1991. Polypeptides comprising affinity tags can further comprise a proteolytic cleavage site between the human PC4 polypeptide and the affinity tag. Such cleavage sites include, for example, thrombin cleavage sites and factor Xa cleavage sites.

TABLE 4

Conservative amino acid substitutions

| Basic:       | arginine       |
|              | lysine         |
|              | histidine      |
| Acidic:      | glutamic acid  |
|              | aspartic acid  |
| Polar:       | glutamine      |
|              | asparagine     |
| Hydrophobic: | leucine        |
|              | isoleucine     |
|              | valine         |
| Aromatic:    | phenylalanine  |
|              | tryptophan     |
|              | tyrosine       |
| Small:       | glycine        |
|              | alanine        |
|              | serine         |
|              | threonine      |
|              | methionine     |

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806–9, 1993; and Chung et al., Proc. Natl. Acad. Sci. USA 90:10145–9, 1993). In a second method, translation is carried out in Xenopus oocytes by microinjection of mutated mRNA and chemically aminoacylated suppressor tRNAs (Turcatti et al., J. Biol. Chem. 271:19991–8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., Biochem. 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395–403, 1993).

A limited number of non-conservative amino acids, amino acids that are not encoded by the genetic code, non-naturally occurring amino acids, and unnatural amino acids may be substituted for human PC4 amino acid residues.

Essential amino acids in the polypeptides of the present invention can be identified according to procedures known in the art, such as site-directed mutagenesis or alanine-scanning mutagenesis (Cunningham and Wells, Science 244, 1081–1085, 1989; Bass et al., Proc. Natl. Acad. Sci. USA 88:4498–502, 1991). In the latter technique, single alanine mutations are introduced at every residue in the molecule, and the resultant mutant molecules are tested for biological activity, as disclosed below, to identify amino acid residues that are critical to the activity of the molecule. See also, Hilton et al., J. Biol. Chem. 271:4699–708, 1996. Sites of human PC4 catalytic domain important for interaction with its substrate(s) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–12, 1992; Smith et al., J. Mol. Biol. 224:899–904, 1992; Wlodaver et al., FEBS Lett. 309:59–64, 1992. The identities of essential amino acids can also be inferred, by one of skill in the art, from analysis of homologies with related prohormone convertases.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed human PC4 DNA and polypeptide sequences can be generated through DNA shuffling as disclosed by Stemmer, *Nature* 370:389–91, 1994; Stemmer, *Proc. Natl. Acad. Sci. USA* 91:10747–51, 1994; and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., cleave a known indicator polypeptide substrate) can be recovered from the host cells and rapidly sequenced using modern equipment. These methods allow the rapid determination of the importance of individual amino acid residues in a polypeptide of interest, and can be applied to polypeptides of unknown structure. Moreover, these mutagenesis methods can be used to engineer proteins that alter reaction kinetics, constrict or expand the substrate specificity, or alter tissue and cellular localization of a polypeptide, such as human prohormone convertase 4.

Using the methods discussed above, one of ordinary skill in the art can prepare a variety of polypeptides that are substantially homologous to residues 1 to 755 of SEQ ID NO: 2 or allelic variants or splice variants thereof and retain the activity of the wild-type protein.

Moreover, using methods described in the art, polypeptide fusions, or hybrid prohormone convertase proteins, are constructed using regions or domains of the inventive human prohormone convertase 4 in combination with those of other known or unknown prohormone convertase proteins (e.g. PC2 and PC1), or heterologous proteins (Sambrook et al., ibid., Altschul et al., ibid., Picard, D., *Cur. Opin. Biology* 5:511–515, 1994, and references therein). These methods allow the determination of the biological importance of larger domains or regions in a polypeptide of interest. Such hybrids alter reaction kinetics, constrict or expand the substrate specificity, or alter tissue and cellular localization of a polypeptide, and can be applied to polypeptides of unknown structure.

Fusion proteins can be prepared by methods known to those skilled in the art. A polynucleotide encoding each component of the fusion protein in the proper reading frame can be generated using known techniques and expressed by the methods described herein. For example, part or all of a domain conferring biological function may be swapped between the human PC4 of the present invention with the corresponding domain from another prohormone convertase, such as PC2 or PC1. Such domains comprise but are not limited to the secretory signal sequence, Homo-A domain, catalytic domain, Homo-B domain, and C-terminal portion of the molecule described herein. One or several domains, such as those described above, can be swapped in this fashion by linking polynucleotide segments in the proper reading frame, creating a DNA polysegment encoding the several domains of the fusion protein. Methods to make such fusion proteins are well known in the art (Sambrook et al., ibid., Altschul et al., ibid., Picard, D., ibid.). Such fusion proteins contain at least one domain from human PC4, and would be expected to have a biological functional profile that is the same or similar to polypeptides of the present invention or other known or unknown prohormone convertase proteins (e.g. PC2 and PC1), depending on the fusion constructed. Moreover, such fusion proteins may exhibit other properties as disclosed above.

For any human PC4 polypeptide, including variants and fusion proteins, one of ordinary skill in the art can readily generate a fully degenerate polynucleotide sequence encoding that variant using the information disclosed herein and set forth in Tables 1 and 2 above.

The polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, NY, 1989, and Ausubel et al., eds., *Current Protocols in Molecular Biology*, John Wiley and Sons, Inc., NY, 1987.

In general, a DNA sequence encoding a human prohormone convertase 4 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a human prohormone convertase 4 polypeptide into the secretory pathway of a host cell, a secretory signal sequence (also known as a leader sequence, prepro sequence or pre sequence) is provided in the expression vector. The secretory signal sequence may be that of the human prohormone convertase 4 polypeptide, or may be derived from another protein targeted to the secretory pathway (e.g., t-PA) or synthesized de novo. The secretory signal sequence is joined to the human prohormone convertase 4 DNA sequence in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention can be used to direct other polypeptides into the secretory pathway. The present invention provides for such fusion polypeptides. A signal fusion polypeptide can be made wherein a secretory signal sequence encoding amino acid residue 1 (Met) to residue 19 (Val) of SEQ ID NO:2 is operably linked to a DNA segment encoding another polypeptide using methods known in the art and disclosed herein. The secretory peptide contained in the resulting fusion polypeptides of the present invention is preferably fused amino-terminally to an additional peptide to direct the additional peptide into the secretory pathway. Such constructs have numerous applications known in the art. For example, these novel secretory signal sequence fusion constructs can direct, for example, the secretion of an active component of a protein not normally fully-secreted, such as a cell-surface receptor, or another non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., Cell 14:725, 1978; Corsaro and Pearson, *Somatic Cell Genetics* 7:603, 1981: Graham and Van der Eb, Virology 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., Focus 15:73, 1993; Ciccarone et al., Focus 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Other preferred cell lines are cultured testicular cells including dolphin DBl.Tes cells (CRL-6258); mouse GC-1 spg cells (CRL-2053); TM3 cells (CRL-1714); TM4 cells (CRL-1715); and pig ST cells (CRL-1746), available from American Type Culture Collection, Rockville, Md. Additional suitable cell lines are known in the art and available from public depositories such as the American Type Culture Collection, Rockville, Maryland. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., J. Biosci. (Bangalore) 11:47–58, 1987. Transformation of insect cells and production of foreign polypeptides therein is disclosed by Guarino et al., U.S. Pat. No. 5,162,222 and WIPO publication Wo 94/06463. Insect cells can be infected with recombinant baculovirus, commonly derived from Autographa californica nuclear polyhedrosis virus (AcNPV). See, King, L.A. and Possee, R.D., The *Baculovirus Expression System: A Laboratory Guide*, London, Chapman & Hall; O'Reilly, D.R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant human PC4 baculovirus utilizes a transposon-based system described by Luckow (Luckow, V.A, et al., *J Virol* 67:4566–79, 1993). This system, which utilizes transfer vectors, is sold in the Bac-to-Bac™ kit (Life Technologies, Rockville, Md.). See, Hill-Perkins, M.S. and Possee, R.D., *J Gen Virol* 71:971–6, 1990; Bonning, B.C. et al., *J Gen Virol* 75:1551–6, 1994; and, Chazenbalk, G. D., and Rapoport, B., *J Biol Chem* 270:1543–9, 1995. In addition, transfer vectors can include an in-frame fusion with DNA encoding an epitope tag at the C- or N-terminus of the expressed human PC4 polypeptide, for example, a Glu-Glu epitope tag (Grussenmeyer, T. et al., *Proc. Natl. Acad. Sci.* 82:7952–4, 1985). Using a technique known in the art, a transfer vector containing human PC4 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses human PC4 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High Five0™ cell line (Invitrogen) derived from *Trichoplusia ni* (U.S. Pat. No. #5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, KS) or Express FiveO™ (Life Technologies) for the *T. ni* cells. The cells are grown up from an inoculation density of approximately $2–5\times10^5$ cells to a density of $1–2\times10^6$ cells at which time a recombinant viral stock is added at a multiplicity of infection (MOI) of 0.1 to 10, more typically near 3. Procedures used are generally described in available laboratory manuals (King, L. A. and Possee, R.D., ibid.; O'Reilly, D.R. et al., ibid.; Richardson, C. D., ibid.). Subsequent purification of the human PC4 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Patents Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a human PC4 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Human prohormone convertase 4 polypeptides prepared according to the present invention are purified using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The cells are harvested, lysed and fractionated. Preferred methods of fractionation include affinity chromatography, Q-Fast Flow Sepharose, MonoQ resin, FPLC, phenyl Sepharose, hydroxyapatite, MonoS and/or S-Sepharose. Proteins can also be purified using an immobilized affinity tag (e.g., polyhistidine, substance P or other polypeptide or protein for which an antibody or other specific binding agent is available). A specific cleavage site may be provided between the protein of interest and the affinity tag. Preferred affinity tags include, for example, a polyhistidine tail, which permits purification of the fusion protein on immobilized nickel (Houchuli et al., *Bio/Technol.* 6:1321–1325, 1988). Truncated forms of the polypeptide, e.g. lacking transmembrane or secretory signal sequence domains, may also be constructed and used to more readily purify catalytically active prohormone convertases (Nakayama, K.

Methods in Enz., 244: 167–175, 1995). In prokaryotic expression systems, a maltose binding protein (MBP) fusion may be advantageously used as an affinity tag. If the protein is to be recovered from the cytoplasm or periplasm of the host cells, the cells are first disrupted, and a crude extract containing the protein is recovered and subjected to further purification steps. Moreover, human prohormone polypeptide substrates and their cleavage products resulting from cleavage by the present invention are purified using methods generally known in the art as disclosed above, with minor changes. For example, secreted proteins, such as cleavage products, are recovered from cell-conditioned media, preferably after concentration of the conditioned media. Selection of particular fractionation steps and the sequence of those steps will be based in part of the type of host cell and the expression system chosen. Such determinations are within the level of ordinary skill in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their structural and biochemical properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

Human PC4 polypeptides can also be used to prepare antibodies that specifically bind to human PC4 epitopes, peptides or polypeptides. The human PC4 polypeptide or a fragment thereof serves as an antigen (immunogen) to inoculate an animal and elicit an immune response. Suitable antigens include the various human PC4 polypeptide domains disclosed herein encoded within SEQ ID NO:2, or a contiguous 9 to 755 amino acid fragment encoded within SEQ ID NO:2. Polyclonal and Monoclonal antibodies generated from this immune response are isolated and purified using methods that are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual*, Second Edition, Cold Spring Harbor, NY, 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats, with a human PC4 polypeptide or a fragment thereof. The immunogenicity of a human prohormone convertase 4 polypeptide may be increased through the use of an adjuvant, such as alum (aluminum hydroxide) or Freund's complete or incomplete adjuvant. Polypeptides useful for immunization also include fusion polypeptides, such as fusions of human prohormone convertase 4 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab' proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to human prohormone convertase 4 protein or a peptide therefrom, and selection of antibody display libraries in phage or similar vectors (for instance, through use of immobilized or labeled human PC4 protein or peptide). Genes encoding polypeptides having potential human PC4 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the human PC4 sequences disclosed herein to identify proteins which bind to human PC4. These "binding proteins" which interact with human PC4 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining levels of polypeptides in tissues; for detecting or quantitating polypeptides as marker of underlying pathology or disease. These binding proteins can also act as human PC4 "antagonists" to block human PC4 cleavage activity in vitro and in vivo.

Antibodies are determined to be specifically binding if: 1) they exhibit a threshold level of binding activity, and 2) they do not significantly cross-react with related polypeptide molecules. First, antibodies herein specifically bind if they bind if they bind to a human prohormone convertase 4 polypeptide, peptide or epitope with an affinity at least 10-fold greater than the binding affinity to control (non-human PC4) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Second, antibodies are determined to specifically bind if they do not significantly cross-react with related polypeptides. Antibodies do not significantly cross-react with related polypeptide molecules, for example, if they detect human PC4 but not known related polypeptides using a standard Western blot analysis (Ausubel et al., ibid.). Examples of known related polypeptides are orthologs (e.g., murine PC4), and paralogs such as other known human prohormone convertases (e.g. PC1 and PC2), or mutant human PC4 polypeptides, and non-mammalian prohormone convertases (e.g., subtilisin, or Kex2). Moreover, antibodies may be "screened against" known related polypeptides to isolate a population that specifically binds to the inventive polypeptides. For example, antibodies raised to human PC4 are adsorbed to related polypeptides adhered to insoluble matrix; antibodies specific to human PC4 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J.W. (eds.), *Academic Press Ltd.*, 1996; Benjamin et al., *Ann. Rev. Immunol.* 2: 67–101, 1984.

A variety of assays known to those skilled in the art can be utilized to detect and purify antibodies which specifically bind to human PC4 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay.

In addition, antibodies can be screened for binding to wild-type versus mutant human PC4 protein or polypeptide. Antibodies to human PC4 may be used for tagging cells that express human PC4; for isolating human PC4 by affinity purification; for diagnostic assays for determining levels of human prohormone convertase 4 polypeptides in cell and tissue lysates in vitro and in vivo; for in situ immunolocalization to determine tissue distribution in vivo; for detecting or quantitating human prohormone convertase 4 proteins as a marker of underlying pathology or disease; in analytical methods employing a flow cytometer or FACS; for screening expression libraries; for generating anti-idiotypic antibodies; and as neutralizing antibodies; or as antagonists to block human PC4 catalytic activity in vitro and in vivo. Methods for utilizing antibodies in this manner are well known in the art. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to human PC4 or fragments thereof may be used in vitro to detect denatured human PC4 or fragments thereof in assays, for example, Western Blots or other assays known in the art.

A testis-specific processing enzyme, such as human prohormone convertase 4, is involved in processing prohormones or binding proteins expressed by testicular cells. Thus, human prohormone convertase 4 may be useful in identifying and determining the biological function of testicular prohormones and identifying novel prohormones as discussed below. In support of the proposition that human PC4 may play a role in fertility, and/or testicular function related to spermatogenesis, is a recent paper describing that homozygous male murine PC4 mutant mice have severely impaired fertility (Mbikay, M., et al., *Proc. Natl. Acad. Sci.*, 94:6842–6846, 1997. Moreover, the authors observed no apparent spermatogenic abnormalities in these mutant mice, and that eggs fertilized by these sperm failed to grow to the blastocyst stage, suggesting not only a role in fertilization but in early embryonic development.

Proteins of the present invention are used to process or partially process known or unknown prohormone polypeptides to their mature or biologically active forms, which may, for example, stimulate proliferation or differentiation of testicular cells. Moreover, proteins of the present invention, their antagonists and agonists, may play a role in male fertility. To test whether human PC4 acts on a substrate, potential prohormone polypeptide substrates may be co-expressed in the same cell as human PC4 or by combined with human PC4 in vitro. Methods to construct such a cell or combine proteins in vitro are known in the art and disclosed herein. Cleavage products result from human PC4 activity on potential prohormone substrates. Activity of the proteins of the present invention can be measured by assaying a biological activity associated with cleavage products of a prohormone precursor polypeptide cleaved by prohormone convertase 4. In addition, if biological activity of a cleavage product cannot be measured, other methods, such as Western Blot, can be used to determine whether human PC4 has cleaved the substrate prohormone.

Polypeptides of the present invention can be used to determine polypeptide prohormone substrates of a human prohormone convertase 4. Using methods well known in the art, a cell can be cultured, into which has been introduced an expression vector that expresses the mature form of human prohormone convertase 4 and co-expresses a test substrate prohormone polypeptide. Cleavage products resulting from cleavage of the test substrate by the human prohormone convertase 4 can be measured by a biological or biochemical assay described herein. Moreover, such a method of determining polypeptide prohormone substrates of a human prohormone convertase 4 polypeptide can be determined in vitro. Isolated or purified human prohormone convertase 4 polypeptide or lysates from cells expressing human prohormone convertase 4 can be combined in vitro with a test substrate polypeptide such as a test substrate prohormone polypeptide or a synthetic polypeptide which contain a dibasic cleavage site. Cleavage products resulting from cleavage of the test substrate prohormone polypeptide by the human prohormone convertase 4 polypeptide can be detected by a biological or biochemical assay described herein.

Various assays may be used to determine the biological activity of cleavage products. For example, proliferation and differentiation can be measured using cultured testicular cells or in vivo by administering prohormone molecules cleaved or processed by polypeptides of the present invention to the appropriate animal model. Cultured testicular cells include dolphin DBl.Tes cells (CRL-6258); mouse GC-1 spg cells (CRL-2053); TM3 cells (CRL-1714); TM4 cells (CRL-1715); and pig ST cells (CRL-1746), available from American Type Culture Collection, Rockville, Md. Assays measuring cell proliferation or differentiation are well known in the art. For example, assays measuring proliferation include such assays as chemosensitivity to neutral red dye (Cavanaugh et al., *Investigational New Drugs* 8:347–354, 1990), incorporation of radiolabeled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988). Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, ESACT, 9th meeting, 1989).

In vivo assays for evaluating the effect of human prohormone convertase 4 on testes polypeptide factors are well known in the art. For example, cleavage products can be injected intraperitoneally for a specific time duration. After the treatment period, animals are sacrificed and testes removed and weighed. Testicles are homogenized and sperm head counts are made (Meistrich et al., *Exp. Cell Res.* 99:72–78, 1976).

Other activities, for example, chemotactic activity, that may be associated with cleavage products of polypeptides processed by a protein of the present invention can also be analyzed. For example, late stage factors in spermatogenesis may be involved in sperm-egg interactions and sperm motility. Assays evaluating such activities are known (Fuchs, *Zentralbl Gynakol* 11:117–120, 1993; Neurwinger et al., *Andrologia* 22:335–339, 1990; Harris et al., *Human Reprod.* 3:856–860, 1988; and Jockenhovel, *Andrologica* 22:171–178, 1990).

In addition, standard biochemical assay techniques, such as western blot, can be used to detect cleavage products resulting from human PC4 processing of substrate prohormones of unknown activity (Sambrook et al., ibid. and Ausubel, et. al., ibid.). Using such methods, cleavage products secreted from cells expressing human PC4 and the test prohormone substrate can be detected by assaying the medium collected from the cells.

Proteins of the present invention are also used in a cell-based screen for modulators of human prohormone convertase 4. Modulators, such as antagonists and agonists, can affect the prohormone convertase in several ways, e.g. catalytic activity, gene expression, or interaction with substrate polypeptides. Such antagonists and agonists would affect the inventive prohormone convertase by respectively decreasing or increasing cleavage activity of human PC4. This increase or decrease is measured by assessing cleavage products from prohormones on which human PC4 acts. In such application, an indicator prohormone substrate, known to be cleaved by polypeptides of the present invention, is expressed in the same cell expressing the human prohormone convertase 4. Methods to construct such a cell are known in the art and disclosed herein. Preferred indicator prohormone polypeptides are secreted from the cell when processed by the prohormone convertase and have a readily measurable biological activity associated with cleavage products. Examples of such activity assays are disclosed above. Antagonists and agonists are identified by screening the resulting cleavage products secreted from the cells after exposure to the presence of various agents discussed below. Changes in the processing of the indicator substrate reflect activities that the agents have on the human PC4 proteins of the present invention by either enhancing or inhibiting the prohormone convertase, relative to control cells not subjected to the agent. For example, relative to the control, an agonist increasing the activity of human PC4 would result in increased cleavage, and hence more biologically active cleavage products from the indicator substrate. Conversely, relative to the control, an antagonist decreasing the activity of human PC4 would result in decreased cleavage, and hence fewer, or potentially no, biologically active cleavage products from the indicator substrate. Sources for agents that may modulate human PC4, and could be evaluated or used in a test sample, include, but are not limited to, any natural or chemical source including but not limited to plant, microbial and fungal extracts, chemical libraries, and combinatorial chemical libraries. Methods of establishing and employing this type of cell-based screening assay are known in the art.

This type of cell-based screening can be used to detect, in a test sample, the presence of a modulator of human prohormone convertase polypeptide activity. A cell which expresses mature human PC4 protein and co-expresses a known indicator prohormone polypeptide substrate, can be cultured in the presence and absence of a test sample. Construction of such a cell can be achieved by methods known in the art and described herein. For example, an expression vector directing the expression of the mature human PC4 protein and an expression vector directing the expression of a known indicator prohormone polypeptide substrate can be introduced into the same cell. The cell in the absence of a test sample serves as a control, against which the activity of the molecule in the presence of a test sample is compared. Using a biological or biochemical assay, levels of cleavage products resulting from cleavage of the substrate by the human prohormone convertase 4 can be compared in the presence and absence of the test sample. From this comparison, the presence of a modulator of human prohormone convertase activity in the test sample can be elucidated as described above.

Polynucleotides of the present invention are also used to detect abnormalities on human chromosome 19 associated with disease or other human traits. The polynucleotides of the present invention map to the 19p13.3 region on human chromosome 19. Detectable chromosomal aberrations at the prohormone convertase gene locus include but are not limited to aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel, et. al., ibid.; Marian, A. J., Chest 108: 255–265, 1995).

The present invention also provides reagents for use in diagnostic applications. For example, the human PC4 gene, a probe comprising human PC4 DNA or RNA, or a subsequence thereof can be used to determine if the human PC4 gene is present on chromosome 19 or if a mutation has occurred. Detectable chromosomal aberrations at the human PC4 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes will generally comprise a polynucleotide linked to a signal-generating moiety such as a radio-labeled nucleotide. In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, PCR Methods and Applications 1:5–16, 1991), ribonuclease protection assays, and other genetic linkage analysis techniques known in the art (Sambrook et al., ibid.; Ausubel et. al., ibid.; A. J. Marian, ibid., 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, PCR Methods and Applications 1:34–38, 1991).

EXAMPLES

Example 1

Cloning of human prohormone convertase 4

A. Summary

Screening of a human testis cDNA library with a murine PC4 cDNA probe revealed an isolated CDNA, clone pSLHPC4–5, that is homologous to murine PC4 cDNA. This cDNA encoded a human prohormone convertase 4 (human PC4).

B. Preparation of human testis cDNA library

A full-length human PC4 CDNA was obtained by screening a λZAP® II (Stratagene, La Jolla, Calif.) human testis cDNA library. The construction of the testis cDNA library was as follows:

The first strand cDNA reaction contained 15 $\mu$l of human testis twice poly d(T)-selected poly(A)$^+$ mRNA (Clontech Laboratories) at a concentration of 1.0 $\mu$g/$\mu$l, and 3 $\mu$l of 20 pmole/$\mu$l first strand primer ZC6091 (SEQ ID NO:5) containing an Xho I restriction site. The mixture was heated at 70° C. for 4 minutes and cooled by chilling on ice. First strand cDNA synthesis was initiated by the addition of 12 $\mu$l of first strand buffer (5×SUPERSCRIPT™ buffer; Life Technologies, Gaithersburg, Md.), 6 $\mu$l of 100 mM dithiothreitol, and 3 $\mu$l of a deoxynucleotide triphosphate solution containing 10 mM each of dTTP, dATP, dGTP and 5-methyl-dCTP (Pharmacia LKB Biotechnology, Piscataway, N.J.) to the RNA-primer mixture. The reaction mixture was incubated at 37° C. for 2 minutes, followed by the addition of 15 $\mu$l of 200 U/$\mu$l RNase H$^-$ reverse transcriptase (SUPERSCRIPT II®; Life Technologies). The efficiency of the first strand synthesis was analyzed in a parallel reaction by the addition of 5 $\mu$Ci of $^{32}$P-αdCTP to a 5 $\mu$l aliquot from one of the reaction mixtures to label the reaction for analysis. The reactions were incubated at 37° C. for 10 minutes, 45° C. for 1 hour, then incubated at 50° C. for 10 minutes. Unincorporated $^{32}$P-αdCTP in the labeled reaction was removed by chromatography on a 400 pore size gel filtration column (Clontech Laboratories). The unicorporated nucleotides and primers in the unlabeled first strand reactions were removed by chromatography on 400 pore size gel filtration column (Clontech Laboratories). The length of labeled first strand cDNA was determined by agarose gel electrophoresis.

The second strand reaction contained 120 μl of the unlabeled first strand cDNA, 36 μl of 5×polymerase I buffer (125 mM Tris: HCl, pH 7.5, 500 mM KCl, 25 mM $MgCl_2$, 50 mM $(NH_4)_2SO_4$)), 2.4 μl of 100 mM dithiothreitol, 3.6 μl of a solution containing 10 mM of each deoxynucleotide triphosphate, 6 μl of 5 mM β-NAD, 3.6 μl of 3 U/μl E. coli DNA ligase (New England Biolabs; Beverly, Mass.), 9 μl of 10 U/μl E. coli DNA polymerase I (New England Biolabs), and 1.8 μl of 2 U/μl RNase H (Life Technologies). A 10 μl aliquot from one of the second strand synthesis reactions was labeled by the addition of 10 μCi $^{32}P$-αdCTP to monitor the efficiency of second strand synthesis. The reactions were incubated at 16° C. for two hours, followed by the addition of 15 μl T4 DNA polymerase (10 U/μl, Boerhinger Mannheim, Indianapolis, Ind.) and incubated for an additional 5 minutes at 16° C. Unincorporated $^{32}P$-αdCTP in the labeled reaction was removed by chromatography through a 400 pore size gel filtration column (Clontech Laboratories) before analysis by agarose gel electrophoresis. The reaction was terminated by the addition of 20 μl 0.5 EDTA and extraction with phenol/chloroform and chloroform followed by ethanol precipitation in the presence of 2.5 M ammonium acetate and 4 μg of glycogen carrier. The yield of cDNA was estimated to be approximately 3 μg from starting mRNA template of 15 μg.

Eco RI adapters were ligated onto the 5' ends of the cDNA described above to enable cloning into an expression vector. A 10 μl aliquot of cDNA (~1.5 μg) and 5 μl of 65 pmole/μl of Eco RI adapter (Pharmacia LKB Biotechnology Inc.) were mixed with 2 μl 10×ligase buffer (660 MM Tris-HCl pH 7.5, 100 mM $MgCl_2$), 2 μl of 10 mM ATP and 1 μl of 15 U/μl T4 DNA ligase (Promega Corp., Madison, Wis.). The reaction was incubated 2 hours at 5° C., two hours at 7.5° C., 2 hours at 10° C., and 10 hours at 12.5° C. The reaction was terminated by incubation at 70° C. for 20 minutes.

To facilitate the directional cloning of the cDNA into a lZapII® vector (Stratagene), the cDNA was digested with Xho I, resulting in a cDNA having a 5' Eco RI cohesive end and a 3' Xho I cohesive end. The Xho I restriction site at the 3' end of the cDNA had been previously introduced using the ZC6091 primer (SEQ ID NO:5). Restriction enzyme digestion was carried out in a reaction mixture containing 20 μl of cDNA described above, 10 μl of 10×H Buffer (Boehringer Mannheim), 69 μl $H_2O$, and 1.0 μl of 40 U/μl Xho I (Boehringer Mannheim). Digestion was carried out at 37° C. for 40 minutes. The reaction was terminated by incubation at 70° C. for 10 minutes and chromatography through a 400 pore size gel filtration column (Clontech Laboratories).

The cDNA was ethanol precipitated, washed with 70% ethanol, air dried and resuspended in 14 μl $H_2O$, 2 μl of ligase buffer (Promega Corp., Madison Wis.), 2 μl T4 polynucleotide kinase (10 U/μl, Life Technologies). Following incubation at 37° C. for 30 minutes, the cDNA was heated to 65° C. for 5 minutes, cooled on ice, and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) and 35 μl 10×β-agarose I buffer (New England Biolabs) was added to the tube, and the agarose was melted by heating to 65° C. for 15 minutes. Following equilibration of the sample to 45° C., 3 μl of 1 U/μl β-agarose I (New England Biolabs) was added, and the mixture was incubated for 60 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 10 μl water.

The resulting cDNA was cloned into the lambda phage vector λZap® II (Stratagene) that was predigested with Eco RI and Xho I and dephosphorylated. Ligation of the cDNA to the λZap® II vector was carried out in a reaction mixture containing 1.0 μl of prepared vector, 1.0 μl of human testis cDNA, 1.0 μl 10×Ligase Buffer (Promega Corp.), 1.0 μl of 10 mM ATP, 5 μl $H_2O$, and 1.0 μl of T4 DNA Ligase at 15 units/μl (Promega Corp.). The ligation mixture was incubated at 5° C.–15° C. overnight in a temperature gradient. After incubation, the ligation mixture was packaged into phage using an in vitro packaging extract (Gigapack® III Gold packaging extract; Stratagene), and the resulting library was titered according to the manufacturer's specifications.

C. Isolation of polynucleotide

The human testis λZap® II library was used to infect E. coli host cells (XL1-Blue™ MRF' strain; Stratagene), and $1.5 \times 10^6$ pfu were plated onto 150-mm NZY plates at a density of ~40,000 pfu/plate. The inoculated plates were incubated overnight at 37° C. Filter plaques lifts were made using nylon membranes (Hybond™-N; Amersham Corp., Arlington Heights, Ill.), according to the procedures provided by the manufacturer. The filters were processed by denaturation in solution containing 1.5 M NaCl and 0.5 M NaOH for 7 minutes at room temperature. The filters were blotted briefly on filter paper to remove excess denaturation solution, followed by neutralization for 5 minutes in 1 M Tris-HCl, pH 7.5, and 1.5 M NaCl. Phage DNA was fixed onto the filters with 1,200 μJoules of UV energy in a UV Crosslinker (Stratalinker®; Stratagene). After fixing, the filters were prehybridized in hybridization solution (5×SSC, 5×Denhardt's solution, 0.2% SDS and 1 mM EDTA). Heat denatured, sheared salmon sperm DNA at a final concentration of 100 μg/ml was added. The filters were prehybridized at 65° C. overnight.

A probe was prepared as a PCR product by using oligonucleotide to amplify the rat prohormone convertase cDNA coding region corresponding to nucleotide 45 to nucleotide 1033 of SEQ ID NO:6. An initial, first-round PCR reaction mixture contained 2 μl of ZC11,808 (SEQ ID NO:7) and 2 μl of ZC11,809 (SEQ ID NO:8), 1 μl of 400 femptogram/μl rat testis cDNA, 1 μl of 10 mM dNTP, 10 μl of 10×Klentaq buffer (Clontech), 83 μl water, and 2 μl Klentaq DNA polymerase (Clontech). The first-round PCR reaction was run as follows: initial 95° C. for 30 seconds; then 30 cycles at 95° C. for 30 seconds, 57° C. for 30 seconds, 68° C. for 2 minutes; followed by 68° C. for 10 minutes. The first-round PCR product was diluted 1:2000 with water. One μl of the diluted first-round PCR product was subjected to a second PCR using nested primers, ZC11,870 (SEQ ID NO:9) and ZC11,871 (SEQ ID NO:10), designed to amplify DNA internal to the first-round PCR product. The second-round PCR reaction was run as follows: initial 95° C. for 30 seconds; then 30 cycles at 95° C. for 30 seconds, 58° C. for 30 seconds, 68° C. for 2 minutes; followed by 68° C. for 10 minutes. The second-round PCR product was gel purified on a 1.5% low melt agarose gel for use as a probe to screen a human testis cDNA library for human PC4.

Twenty-five nanograms PCR product was radiolabeled with a $^{32}P$-dCTP by random priming using the MEGAPRIME™ DNA Labeling System (Amersham), according to the manufacturer's specifications. The prehybridization solution was replaced with fresh hybridization solution containing 6.5×10⁵ cpm/ml labeled probe and allowed to hybridize overnight at 60° C. After hybridization, the hybridization solution was removed, and the filters were rinsed in a wash solution containing 1×SSC, 0.25% SDS and 1 mM EDTA at 45° C. The filters were placed on autoradiograph film and exposed at −70° C. with intensifying screens for 96 hours.

Examination of the autoradiographs revealed multiple regions that hybridized with the labeled probe. Agar plugs were picked from 39 regions for purification. Each agar plug was soaked overnight in 0.5 ml of SM containing 1% (v/v) chloroform (Sambrook et al. *Molecular Cloning: A Laboratory Manual*, 2nd ed., Cold Spring Harbor Laboratory Press, Cold Spring Harbor, NY, 1989). After incubation, the phage from each plug were diluted 1:1000 in SM. Aliquots of 50 μl were plated on *E. coli* XL-1 Blue™ MRF' cells. The plates were incubated overnight at 37° C., and filter lifts were prepared, prehybridized, hybridized, washed and autoradiographed as described above. Examination of the resulting autoradiographs revealed positive signals on 10 filter lifts. Agar plugs were picked from these regions and were subjected to an additional round of plaque purification.

The plasmids were excised using an ExASSIST/SOLR™ system (Stratagene), according to the manufacturer's specification. These plasmids were amplified by PCR for insert size determination and sequencing. A clone, designated pSLHPC4–5, was shown to contain the sequence shown in SEQ ID NO: 1.

Example 2

Tissue Distribution

A probe was prepared from the full length coding sequence of pSLHPC4–5 and used to probe Human Multiple Tissue Northern Blots (Clontech). The Northern analysis revealed a band at approximately 2.8 Kb that was only present in testis.

Example 3

PCP-Based Chromosomal Mapping of the human PC4 Gene

Human PC4 was mapped to chromosome 19 using the commercially available "GeneBridge 4 Radiation Hybrid Panel" (Research Genetics, Inc., Huntsville, Ala.). The GeneBridge 4 Radiation Hybrid Panel contains DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's map of the human genome (the "WICGR" human genomic map) which was constructed with the GeneBridge 4 Radiation Hybrid Panel.
B.

For the mapping of human PC4 with the "GeneBridge 4 RH Panel", 20 μl PCR reactions were set up in a 96-well microtiter plate (Stratagene) and used in a "RoboCycler Gradient 96" thermal cycler (Stratagene). Each of the 95 PCR reactions consisted of 2 μl 10×KlenTaq PCR reaction buffer (Clontech Laboratories, Inc., Palo Alto, Calif.), 1.6 μl dNTPs mix (2.5 mM each, Perkin-Elmer, Foster City, Calif.), 1 μl sense primer, ZC13,557 (SEQ ID NO:11), 1 μl antisense primer, ZC13,558 (SEQ ID NO:12), 2 μl "Redi-Load" (Research Genetics, Inc., Huntsville, Ala.), 0.4 μl 50×Advantage KlenTaq Polymerase Mix (Clontech Laboratories, Inc.), 25 ng of DNA from an individual hybrid clone or control and ddH₂O for a total volume of 20 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 68° C. and 1.5 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that human PC4 maps 10.54 cR_3000 distal from the chromosome 19 framework marker IB1264 on the WICGR radiation hybrid map. This positions human PC4 in the 19p13.3 region on the integrated LDB chromosome 19 map (The Genetic Location Database, University of Southhampton, www server: http://cedar.genetics.soton.ac.uk/public_html/).

Example 4

Construction of human PC4 Mammalian Expression Vector PPC4–5/pHZ1

An expression vector was prepared for expressing the human PC4 polypeptide in mammalian cells. The mammalian expression vector pHZ1 has the neomycin gene under control of the SV40 early promoter, SV40 polyadenylation site, a multiple cloning site (polylinker) to insert the gene of interest under control of the metallothionine (MT-1) promoter, and the human growth hormone (hGH) polyadenylation site. The expression vector is deposited with the American Type Culture Collection, 12301 Parklawn Drive, Rockville, Md.

Human PC4 was subcloned into the EcoRI/XbaI site in the PHZ1 polylinker. The vector fragment was prepared by cleaving PHZ1 with EcoRI and XbaI (Boehringer-Mannheim) followed by fragment isolation via Qiaquick™ column (Qiagen). A 1644 bp fragment (5' fragment) was excised from the human PC4 clone in Example 1 with restriction enzymes EcoRI and AatII which gives the 5' end of the human PC4 sequence including 5' UTRs as disclosed in SEQ ID NO:1. An approximately 681 bp PCR fragment was PCR-amplified from the human PC4 clone in Example 1 with primer ZC13,359 (SEQ ID NO:13) which spans the human PC4 AatII site and primer ZC13,358 (SEQ ID NO:14) which contains a XbaI site, giving the 3' end of the human PC4 sequence including 3' UTRs as disclosed in SEQ ID NO:1. The PCR reaction conditions were: one cycle at 94° C. for 1 minute; then 35 cycles at 94° C. for 30 seconds, 50° C. for 20 seconds, 72° C. for 30 seconds; followed by one cycle at 72° C. for 10 minutes. The PCR product was cleaved with AatII and XbaI, and fragment purified as described above, generating the 681 bp PCR fragment (3' fragment).

The excised 5' fragment and 3' fragment DNA was subcloned into the pHZ1 vector fragment. Approximately 20 nanograms of the Eco RI/AatII digested human PC4 5' fragment, approximately 20 nanograms of the AatII/XbaI digested human PC4 3' fragment, and approximately 40 ng of the corresponding vector fragment were ligated 5 hours at room temperature, under standard ligation reaction buffer conditions. Of this ligation reaction, 1 μl was electroporated into 25 μl DH1OB competent cells (GIBCO BRL, Gaithersburg, Md.) according to manufacturer's instructions, plated onto LB plates containing 100 mg/ml ampicillin and incubated overnight at 37° C.

Colonies were screened by PCR using primers ZC12,634 (SEQ ID NO:15) and ZC12,945 (SEQ ID NO:16) under the following PCR conditions: one cycle at 94° C. for 1 minute; then 25 cycles at 94° C. for 20 seconds, 50° C. for 30 seconds, 72° C. for 1 minute; followed by one cycle at 72° C. for 10 minutes. The insert sequence of positive clones were verified by sequence analysis. Large scale plasmid preparation was done using a QIAGEN® Maxi prep kit (Qiagen) according to manufacturer's instructions.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide encoding a human prohormone convertase 4 polypeptide comprising a sequence of amino acid residues that is at least 90% identical to an amino acid sequence selected from the group consisting of:
   (a) the amino acid sequence as shown in SEQ ID NO:2 from amino acid number 114 (Ser) to amino acid number 443 (Ala);
   (b) the amino acid sequence as shown in SEQ ID NO:2 from amino acid number 114 (Ser) to amino acid number 755 (Thr);
   (c) the amino acid sequence as shown in SEQ ID NO:2 from amino acid number 20 (Arg) to amino acid number 755 (Thr); and
   (d) the amino acid sequence as shown in SEQ ID NO:2 from amino acid number 1 (Met) to amino acid number 755 (Thr), and
   wherein the prohormone convertase polypeptide encoded by the polynucleotide sequence has prohormone convertase activity.

2. An isolated polynucleotide according to claim 1, wherein the polynucleotide is selected from the group consisting of:
   (a) a polynucleotide sequence as shown in SEQ ID NO:1 from nucleotide 400 to nucleotide 1389;
   (b) a polynucleotide sequence as shown in SEQ ID NO:1 from nucleotide 400 to nucleotide 2325;
   (c) a polynucleotide sequence as shown in SEQ ID NO:1 from nucleotide 118 to nucleotide 2325; and
   (d) a polynucleotide sequence as shown in SEQ ID NO:1 from nucleotide 61 to nucleotide 2325.

3. An isolated polynucleotide sequence according to claim 1, wherein the polynucleotide comprises nucleotide 1 to nucleotide 2265 of SEQ ID NO:3.

4. An isolated polynucleotide according to claim 1, wherein the prohormone convertase 4 polypeptide is at least 90% identical to a sequence of amino acid residues as shown in SEQ ID NO:2 from amino acid number 20 (Arg) to amino acid number 755 (Thr), and
   wherein the prohormone convertase polypeptide encoded by the polynucleotide sequence has prohormono convertase 4 activity.

5. An expression vector comprising the following operably linked elements:
   a transcription promoter;
   a DNA segment encoding a prohormone convertase polypeptide that is at least 90% identical to an amino acid sequence as shown in SEQ ID NO:2 from amino acid number 20 (Arg) to amino acid number 755 (Thr); and
   a transcription terminators, and
   wherein the prohormone convertase polypeptide encoded by the DNA segment has prohormone convertase 4 activity.

6. An expression vector according to claim 5, further comprising a secretory signal sequence operably linked to the DNA segment.

7. A cultured cell into which has been introduced an expression vector according to claim 5, wherein the cell expresses a polypeptide encoded by the DNA segment.

8. A DNA construct encoding a fusion protein, the DNA construct comprising:
   a first DNA segment encoding a polypeptide comprising a sequence of amino acid residues selected from the group consisting of:
      (a) the amino acid sequence of SEQ ID NO: 2 from residue number 1 (Met), to residue number 21 (Pro);
      (b) the amino acid sequence of SEQ ID NO: 2 from residue number 20 (Arg), to residue number 113 (Arg);
      (c) the amino acid sequence of SEQ ID NO: 2 from residue number 114 (Ser), to residue number 443 (Ala);
      (d) the amino acid sequence of SEQ ID NO: 2 from residue number 444 (Arg), to residue number 561 (Tyr);
      (e) the amino acid sequence of SEQ ID NO: 2 from residue number 562 (Tyr), to residue number 755 (Thr);
      (f) the amino acid sequence of SEQ ID NO: 2 from residue number 114 (Ser), to residue number 755 (Thr); and
      (g) the amino acid sequence of SEQ ID NO: 2 from residue number 20 (Arg), to residue number 755 (Thr); and
   at least one other DNA segment encoding an additional polypeptide,
   wherein the first and other DNA segments are connected in-frame; and
   encode the fusion protein.

9. A method of producing a human prohormone convertase 4 polypeptide comprising:
   culturing a cell according to claim 7; and
   isolating the human prohormone convertase 4 polypeptide produced by the cell.

10. An isolated polynucleotide according to claim 1, comprising a sequence of amino acid residues selected from the group consisting of:
   (a) the amino acid sequence as shown in SEQ ID NO:2 from amino acid number 114 (Ser) to amino acid number 443 (Ala);
   (b) the amino acid sequence as shown in SFQ ID NO:2 from amino acid number 114 (Ser) to amino acid number 755 (Thr);
   (c) the amino acid sequence as shown in SEQ ID NO:2 from amino acid number 20 (Arg) to amino acid number 755 (Thr); and
   (d) the amino acid sequence as shown in SEQ ID NO:2 from amino acid number 1 (Met) to amino acid number 755 (Thr).

11. An isolated polynucleotide according to claim 4, wherein the prohormone convertase 4 polypeptide consists of a sequence of amino acid residues as shown in SEQ ID NO:2 from amino acid number 20 (Arg) to amino acid number 755 (Thr).

12. An expression vector according to claim 5, comprising the following operably linked elements:
   a transcription promoter;
   a DNA segment encoding a prohormone convertase polypeptide comprising an amino acid sequence as shown in SEQ ID NO:2 from amino acid number 20 (Arg) to amino acid number 755 (Thr); and
   a transcription terminator.

* * * * *